(12) United States Patent
Pennathur et al.

(10) Patent No.: US 10,352,899 B2
(45) Date of Patent: Jul. 16, 2019

(54) SYSTEM AND METHOD FOR DETECTION OF SILVER

(71) Applicants: ALVEO Technologies Inc., Lafayette, CA (US); The Regents of the University of California, Oakland, CA (US)

(72) Inventors: Sumita Pennathur, Goleta, CA (US); Peter Joseph Crisalli, Goleta, CA (US); Ronald Phillip Chiarello, Lafayette, CA (US)

(73) Assignees: ALVEO Technologies Inc., Lafayette, CA (US); The Regents of the University of California, Oakland, CA (US)

( * ) Notice: Subject to any disclaimer, the term of this patent is extended or adjusted under 35 U.S.C. 154(b) by 291 days.

(21) Appl. No.: 14/507,820

(22) Filed: Oct. 6, 2014

(65) Prior Publication Data

US 2016/0097741 A1 Apr. 7, 2016

(51) Int. Cl.
*G01N 27/49* (2006.01)
*G01N 27/02* (2006.01)
(Continued)

(52) U.S. Cl.
CPC .............. *G01N 27/49* (2013.01); *B82Y 30/00* (2013.01); *G01N 27/00* (2013.01); *G01N 27/02* (2013.01);
(Continued)

(58) Field of Classification Search
CPC ........ G01R 17/02; G01N 27/00; G01N 27/02; G01N 27/26; G01N 27/49
See application file for complete search history.

(56) References Cited

U.S. PATENT DOCUMENTS 5,456,811 A * 10/1995 Edwards ................ G01N 27/38
204/402
5,589,136 A 12/1996 Northrup et al.
(Continued)

FOREIGN PATENT DOCUMENTS

EP 2003446 12/2008

OTHER PUBLICATIONS

Liu, Lei et al.; Fluorescence "Turn On" Chemosensors for Ag+ and Hg2+ Based on Tetraphenylethylene Motif Featuring Adenine and Thymine Moieties; organic letters; Sep. 12, 2008; vol. 10, No. 20; 4581-4584.*

(Continued)

*Primary Examiner* — Edward J. Schmiedel
(74) *Attorney, Agent, or Firm* — Knobbe, Martens, Olson & Bear LLP

(57) ABSTRACT

Embodiments provide silver detection systems and methods for detecting the presence of silver ions in one or more samples. In a detection method, a sample and TPEA2 molecules are introduced into a channel. A first potential difference is applied across the length of the channel in a first direction, and a first electrical property value is detected. Subsequently, a second potential difference is applied across the length of the channel in a second opposite direction, and a second electrical property value is detected. Presence or absence of silver ions in the channel is determined based on a comparison between the first and second electrical property values.

17 Claims, 21 Drawing Sheets

(51) Int. Cl.
*G01R 17/02* (2006.01)
*G01N 27/00* (2006.01)
*G01N 27/26* (2006.01)
*B82Y 30/00* (2011.01)
*G01N 27/06* (2006.01)

(52) U.S. Cl.
CPC ............. *G01N 27/06* (2013.01); *G01N 27/26* (2013.01); *G01R 17/02* (2013.01)

(56) References Cited

U.S. PATENT DOCUMENTS

| | | |
|---|---|---|
| 6,403,367 B1 | 6/2002 | Cheng et al. |
| 6,524,532 B1 | 2/2003 | Northrup |
| 6,576,459 B2 | 6/2003 | Miles et al. |
| 6,602,473 B1 | 8/2003 | Northrup |
| 6,699,713 B2 | 3/2004 | Benett et al. |
| 6,875,602 B2 | 4/2005 | Gutierrez |
| 7,062,385 B2 | 6/2006 | White et al. |
| 7,135,294 B2 | 11/2006 | Lee et al. |
| 7,157,050 B2 | 1/2007 | Yazawa et al. |
| 7,172,896 B2 | 2/2007 | Cheng et al. |
| 7,483,805 B2 | 1/2009 | Sparks et al. |
| 7,708,944 B1 | 5/2010 | Sadik et al. |
| 7,915,030 B2 | 5/2011 | Inoue et al. |
| 8,078,408 B2 | 12/2011 | Albert et al. |
| 8,106,428 B2 | 1/2012 | Koh et al. |
| 8,133,671 B2 | 3/2012 | Williams et al. |
| 8,173,077 B2 | 5/2012 | Korampally et al. |
| 8,283,155 B2 | 10/2012 | Holmes et al. |
| 8,308,929 B2* | 11/2012 | West .................. C23C 18/161 204/400 |
| 8,329,453 B2 | 12/2012 | Battrell et al. |
| 8,354,074 B2 | 1/2013 | Silverbrook et al. |
| 8,370,070 B2 | 2/2013 | Fernandez |
| 8,383,064 B2 | 2/2013 | Azimi et al. |
| 8,414,844 B2 | 4/2013 | Sadik et al. |
| 8,431,389 B2 | 4/2013 | Battrell et al. |
| 8,431,390 B2 | 4/2013 | Jovanovich et al. |
| 8,480,980 B2 | 7/2013 | Yoo |
| 8,524,490 B2 | 9/2013 | Lipscomb et al. |
| 8,614,059 B2 | 12/2013 | Young |
| 8,716,007 B2 | 5/2014 | Battrell et al. |
| 8,841,076 B2 | 9/2014 | Holmes et al. |
| 8,865,075 B2 | 10/2014 | Guzman |
| 8,865,401 B2 | 10/2014 | Young et al. |
| 8,883,487 B2 | 11/2014 | Collier et al. |
| 8,951,472 B2 | 2/2015 | Kellner et al. |
| 8,956,858 B2 | 2/2015 | Dineen et al. |
| 9,029,168 B2 | 5/2015 | McAlpine et al. |
| 2002/0067174 A1 | 6/2002 | McAllister |
| 2004/0132059 A1 | 7/2004 | Scurati et al. |
| 2004/0166504 A1 | 8/2004 | Rossier et al. |
| 2004/0170530 A1 | 9/2004 | Hefti |
| 2005/0274612 A1 | 12/2005 | Segawa |
| 2006/0176179 A1 | 8/2006 | Skorpik et al. |
| 2007/0141605 A1 | 6/2007 | Vann et al. |
| 2007/0158766 A1* | 7/2007 | Lieber ................... B82Y 10/00 257/414 |
| 2007/0298487 A1 | 12/2007 | Bachur et al. |
| 2008/0308846 A1* | 12/2008 | Shim .................. G01N 27/4145 257/253 |
| 2009/0061450 A1 | 5/2009 | Hunter |
| 2010/0041056 A1 | 2/2010 | Kinnon et al. |
| 2010/0084286 A1* | 4/2010 | West ..................... C23C 18/161 205/775 |
| 2010/0105035 A1 | 4/2010 | Hashsham et al. |
| 2010/0075312 A1 | 5/2010 | Davies et al. |
| 2010/0200400 A1 | 8/2010 | Revol-Cavalier |
| 2010/0216225 A1 | 8/2010 | Dyer et al. |
| 2010/0240044 A1 | 9/2010 | Kumar et al. |
| 2010/0243449 A1 | 9/2010 | Oliver |
| 2011/0039261 A1 | 2/2011 | Hillebrand et al. |
| 2011/0068015 A1* | 3/2011 | Park .................. G01N 27/4145 205/792 |
| 2011/0091879 A1 | 4/2011 | Hillebrand et al. |
| 2011/0136104 A1 | 6/2011 | Pregibon et al. |
| 2011/0165572 A1 | 7/2011 | O'Halloran |
| 2011/0244467 A1 | 10/2011 | Haswell |
| 2011/0312073 A1 | 12/2011 | Silverbrook et al. |
| 2011/0312074 A1 | 12/2011 | Azimi |
| 2011/0312610 A1 | 12/2011 | Azimi et al. |
| 2011/0312657 A1 | 12/2011 | Azimi et al. |
| 2011/0312683 A1 | 12/2011 | Silverbrook et al. |
| 2011/0312791 A1 | 12/2011 | Silverbrook et al. |
| 2011/0312826 A1 | 12/2011 | Silverbrook et al. |
| 2011/0312841 A1 | 12/2011 | Silverbrook et al. |
| 2011/0318728 A1 | 12/2011 | Phan et al. |
| 2012/0052562 A1 | 3/2012 | Silverbrook et al. |
| 2012/0053088 A1 | 3/2012 | Azimi et al. |
| 2012/0058547 A1 | 3/2012 | Hsing et al. |
| 2012/0064523 A1 | 3/2012 | Ecker et al. |
| 2012/0129709 A1* | 5/2012 | Zhang .................. C12Q 1/6825 506/9 |
| 2012/0150004 A1 | 6/2012 | Currie et al. |
| 2012/0183965 A1 | 6/2012 | Ward et al. |
| 2012/0329144 A1 | 12/2012 | Kwak |
| 2013/0011912 A1 | 1/2013 | Battrell et al. |
| 2013/0029333 A1 | 1/2013 | Son et al. |
| 2013/0079236 A1 | 3/2013 | Holmes |
| 2013/0085680 A1 | 4/2013 | Arlen et al. |
| 2013/0101990 A1 | 4/2013 | Handique et al. |
| 2013/0109021 A1 | 5/2013 | Hwang |
| 2013/0109022 A1 | 5/2013 | Hwang |
| 2013/0115685 A1 | 5/2013 | Holmes et al. |
| 2013/0183750 A1 | 7/2013 | Sadik et al. |
| 2013/0244898 A1 | 9/2013 | Burd et al. |
| 2013/0252320 A1 | 9/2013 | Burd et al. |
| 2013/0267016 A1 | 10/2013 | Niemz et al. |
| 2013/0273528 A1 | 10/2013 | Ehrenkranz |
| 2013/0280725 A1 | 10/2013 | Ismagilov et al. |
| 2013/0309676 A1 | 11/2013 | Layne |
| 2013/0309679 A1 | 11/2013 | Ismagilov et al. |
| 2014/0072962 A1 | 3/2014 | Kelley et al. |
| 2014/0099636 A1 | 4/2014 | Lee |
| 2014/0170646 A1 | 6/2014 | Kelley et al. |
| 2014/0186935 A1 | 7/2014 | Yoo |
| 2014/0206562 A1 | 7/2014 | McCormack et al. |
| 2014/0287414 A1 | 9/2014 | Chung et al. |
| 2014/0329244 A1 | 11/2014 | Ding et al. |
| 2014/0335527 A1 | 11/2014 | Goel |
| 2014/0349298 A1 | 11/2014 | Stanchina et al. |
| 2014/0349381 A1 | 11/2014 | Battrell et al. |
| 2015/0041315 A1 | 2/2015 | Jack |
| 2015/0041317 A1 | 2/2015 | Chan |
| 2015/0041328 A1 | 2/2015 | Chan |
| 2015/0041336 A1 | 2/2015 | Chan |
| 2015/0044679 A1 | 2/2015 | Jack |
| 2015/0045254 A1* | 2/2015 | Jack ..................... C12Q 1/6825 506/9 |
| 2015/0064707 A1 | 3/2015 | Collier |
| 2015/0093304 A1 | 4/2015 | Guzman |
| 2015/0104792 A1 | 4/2015 | Mazumdar et al. |
| 2015/0111287 A1 | 4/2015 | Rawle |
| 2015/0141264 A1 | 5/2015 | Jung et al. |
| 2015/0141268 A1 | 5/2015 | Rothberg et al. |
| 2016/0097739 A1 | 4/2016 | Pennathur |
| 2016/0097740 A1* | 4/2016 | Pennathur ............... G01N 27/49 205/789 |
| 2016/0097742 A1 | 4/2016 | Pennathur |
| 2016/0130639 A1 | 5/2016 | Pennathur |

OTHER PUBLICATIONS

Roya Mohammad Zadeh Kakhki, et al.; A simple conductometric method for trace level determination of brilliant green in water based on β-cyclodextrin and silver nitrate and determination of their thermodynamic parameters, Arabian Journal of Chemistry, vol. 7, Issue 6, Sep. 20, 2011 (Year: 2011).*

Gillen, Keith, et al.; Binding Of Silver Ion by Adenine and Substituted Adenines; Journal of the American Chemical Society 1964 86 (14), 2792-2796 (Year: 1964).*

(56) References Cited

OTHER PUBLICATIONS

Stephen Mifsud; ID of Silver Cations by Precipitation Reactions; Marz Kreations; http://www.marz-kreations.com/Chemistry/Cation-ID/162-CationID.html; Jul. 21, 1998 (Year: 1998).*
Standard Reduction Potentials of Half-Cells; https://www.ed.gov.nl.ca/edu/k12/evaluation/chem3202/standardreductionpotentials.pdf; accessed and printed Aug. 13, 2018 (Year: 2018).*
G.B. David, et al.; A method of silvering the 'Golgi Apparatus' (Nissl Network) in Paraffin Sections of the Central Nervous system of Vertebrates; https://pdfs.semanticscholar.org/8c1a/383c2d5b8b7d40eab188c7358deb21d62dbe.pdf; accessed and printed Aug. 13, 2018; pp. 207-221 (Year: 2018).*
"Conductivity Theory and Practice" Radiometer analytical SAS, 2004.
Backer et al., "Planar and 3D interdigitated electrodes for biosensing applications: The impact of a dielectric barrier on the sensor properties" Phys. Status Solidi A, 1-7 (2014).
Bhat, "Salinity (conductivity) sensor based on parallel plate capacitors" Thesis, 2005, Univ. South Florida.
Brito-Neto et al., "Understanding Capacitively Coupled Contactless Conductivity Detection in Capillary and Microchip Electrophoresis. Part 1. Fundamentals" Electroanalysis 2005, 17, No. 13.
Coltro et al., "Capacitively coupled contactless conductivity detection on microfluidic systems—ten years of development" Anal. Methods, 2012, 4, 25.
Coltro et al., "Microfluidic devices with integrated dual-capacitively coupled contactless conductivity detection to monitor binding events in realtime" Sensors and Actuators B 192 (2014) 239-246.
Hilland "Simple sensor system for measuring the dielectric properties of saline solutions" Meas. Sci. Technol. 8 (1997) 901-910.
Kuban et al., "A review of the recent achievements in capacitively coupled contactless conductivity detection" Analytica Chimica Acta 607 (2008) 15-29.
Kuban et al., "Contactless conductivity detection for analytical techniques: Developments from 2010 to 2012" Electrophoresis 2013, 34, 55-69.
Kuban et al., "Effects of the cell geometry and operating parameters on the performance of an external contactless conductivity detector for microchip electrophoresis" Lab Chip, 2005, 5, 407-415.
Lasia, A., Electrochemical Impedance Spectroscopy and Its Applications, Modern Aspects of Electrochemistry, B. E. Conway, J. Bockris, and R.E. White, Edts., Kluwer Academic/Plenum Publishers, New York, 1999, vol. 32, p. 143-248.
Lima et al., "Contactless conductivity biosensor in microchip containing folic acid as bioreceptor" Lab Chip, 2012, 12, 1963-1966.
Lima et al., "Highly sensitive contactless conductivity microchips based on concentric electrodes for flow analysis" Chem. Commun., 2013, 49, 11382.
MacDonald and Johnson, "Fundamentals of impedance spectroscopy" Chapter1, Impedance Spectroscopy, Second Edition, edited by Evgenij Barsoukov and J. Ross Macdonald (2005).
Mahabadi et al., "Capacitively coupled contactless conductivity detection with dual top-bottom cell configuration for microchip electrophoresis". Electrophoresis 2010, 31, 1063-1070.
Opekar et al., "Contactless Impedance Sensors and Their Application to Flow Measurements" Sensors 2013, 13, 2786-2801.
Pumera et al., "Contactless Conductivity Detector for Microchip Capillary Electrophoresis" Anal. Chem. 2002, 74, 1968-1971.
Pumera, "Contactless conductivity detection for microfluidics: Designs and applications" Talanta 74 (2007) 358-364.
Raistrick et al., "Theory" Chapter2, Impedance Spectroscopy, Second Edition, edited by Evgenij Barsoukov and J. Ross Macdonald (2005).
Ramos et al., "A Four-Terminal Water-Quality -Monitoring Conductivity Sensor". IEEE Transactions on Instrumentation and Measurement, vol. 57, No. 3, Mar. 2008.
Rana et al., "Comparison of Planar and 3-D Interdigitated Electrodes as Electrochemical Impedance Biosensors" Electroanalysis 2011, 23, No. 10, 2485-2490.
Rana et al., "Impedance spectra analysis to characterize interdigitated electrodes as electrochemical sensors" Electrochimica Acta 56 (2011) 8559-8563.
Simon et al., "Label-Free Detection Of Dna Amplification In Droplets Using Electrical Impedance" 15th International Conference on Miniaturized Systems for Chemistry and Life Sciences Oct. 2-6, 2011, Seattle, Washington, USA, pp. 1683-1685.
Tanyanyiwa et al., "High-Voltage Capacitively Coupled Contactless Conductivity Detection for Microchip Capillary Electrophoresis" Anal. Chem. 2002, 74, 6378-6382.
Tomsic et al., "Conductivity of Magnesium Sulfate in Water from 5 to 35° C. and from Infinite Dilution to Saturation" Journal of Solution Chemistry, vol. 31, No. 1, Jan. 2002.
Wang et al., "Microchip enzymatic assay of organophosphate nerve agents" Analytica Chimica Acta 505 (2004) 183-187.
Wang et al., "Towards disposable lab-on-a-chip: Poly(methylmethacrylate) microchip electrophoresis device with electrochemical detection" Electrophoresis 2002, 23, 596-601.
Zhang et al., "Monitoring the progression of loop-mediated isothermal amplification using conductivity" Analytical Biochemistry 466 (2014) 16-18.
Anderson, M.B. et al, "Surface-dependent chemical equilibrium constants and capacitances for bare and 3-10 cyanopropyldimethylchlorosilane coated silica nanochannels" J. Colloid Interface Sci. 353:301-310 (2011).
Hsieh, K., et al, "Rapid, Sensitive and Quantitative Detection of Pathogenic DNA at the Point of Care via Microfluidic Electrochemical Quantative Loop-Mediated Isothermal Amplification (MEQ-LAMP)" Angew Chem Intl Ed Engl 51(20):4896-4900 (2012).
Jenson, K.L., et al., "Hydronium-domination ion transport in carbon-dioxide-saturated electrolytes at low salt concentrations in nanochannels" Phys. Review E. 83:5 (2011), 056307.
Mori, Y, et al, "Detection of Loop-Mediated Isothermal Amplification Reaction by Turbidity Derived from Magnesium Pyrophosphate Formation" Biochemical and Biophysical Research Communications 289:150-154 (2001).
Mori, Y., et al, "Real-time turbidimetry of LAMP reaction for quantifying template DNA" J. Biochem Biphys Methods 59:145-157 (2004).
Nagamine, K., et al, "Accelerated reaction by loop-mediated isothermal amplification using loop primers" Molecular and Cellular Probes 16:223-229 (2002).
Nakamura, N, et al, "Detection of Six Single-Nucleotide Polymorphisms Associated with Rheumatoid Arthritis by a Loop-Mediated Isothermal Amplification Method and an Electrochemical DNA Chip" Anal Chem 79:9484-9493 (2007).
Notomi, T., et al, "Loop-mediated isothermal amplification of DNA" Nucleic Acids Res 25(12): i-vii (2000).
Pennathur, S., et al, "Low Temperature Fabrication and Surface Modification Methods for Fused Silica Micro- and Nanochannels," MRS Proceedings, 1659:15-26 (2014). doi:10.1557/opl.2014.32.
Rosenfeld, T., et al, Lab on a Chip: 100-fold sample on paper-based microfluidic devices, Lab Chip http:pubs.rsc.org/en/content/articlelanding/2014/lc/c41c00734d (2014).
Schwartz, O., et at, "Microfluidic Assay for Continuous Bacteria Detection Using Antimicrobial Peptides and Isotachophoresis" Anal Chem 86:10106-10113 (2014).
Tomita, N., et al, "Loop-mediated isothermal amplification (LAMP) of gene sequences and simple visual detection of products" Nature Protocols 3(5):877-822 (2008).
Xie, S., et al, "Development of an electrochemical method for Ochratoxin A detection based on aptamer and loop-mediated isothermal amplification" Biosensors and Bioeletronics 55:324-329 (2014).

\* cited by examiner

SYSTEM AND METHOD FOR DETECTION OF SILVER

CROSS-REFERENCE TO RELATED APPLICATIONS

The present application is related to the following co-owned patent applications filed concurrently with the present application: (i) U.S. patent application Ser. No. 14/507,825, titled "System for Detection of Analytes," (ii) U.S. patent application Ser. No. 14/507,828, titled "Method for Detection of Analytes," and (iii) U.S. patent application Ser. No. 14/507,818, titled "System and Method for Detection of Mercury." The entire contents of each of the above-referenced patent applications are expressly incorporated herein by reference.

BACKGROUND

Sensitive and selective detection of chemical and biological analytes has important implications for medical and environmental testing and research. Hospitals and laboratories, for example, routinely test biological samples to detect potentially toxic substances, such as mercury and silver, in heavy metal poisoning diagnosis. Similarly, measurement of biomolecules, such as nucleic acids, is a foundation of modern medicine and is used in medical research, diagnostics, therapy and drug development.

Nanopore sequencing technology is a conventional method of detecting nucleic acid molecules. The concept of nanopore sequencing utilizes a nanopore aperture, which is a small hole or pore that extends transversely through a lipid bilayer membrane, i.e., through the depth or thickness dimension of the membrane. Nanopore sequencing involves causing a nucleotide to travel through a nanopore in the membrane, i.e., to travel between the top surface and the bottom surface of the membrane along the depth or thickness dimension of the membrane. A potential difference may be applied across the depth or thickness dimension of the membrane to force the nucleotide to travel through the nanopore. Physical changes in the environment of the nucleotide (for example, electric current passing through the nanopore) are detected as the nucleotide traverses through the nanopore. Based on the detected changes in the electrical current, the nucleotide may be identified and sequenced.

Areas for improving and broadening the scope of conventional systems and techniques of silver detection have been identified, and technical solutions have been implemented in exemplary embodiments.

SUMMARY

In accordance with one exemplary embodiment, a method is provided for detecting the presence or absence of silver ions in a sample. The method includes introducing a sample into a channel, the channel having a length and a width, the length substantially greater than the width; measuring an electrical property value of an electrical property along at least a portion of the length of the channel after the sample is introduced into the channel; accessing a reference electrical property value, the reference electrical property value associated with the electrical property of the channel along at least a portion of the length of the channel prior to introduction of the sample into the channel; comparing the measured electrical property value and the reference electrical property value; and determining whether silver ions are present in the channel based on the comparison between the measured electrical property value and the reference electrical property value.

In accordance with another exemplary embodiment, a method is provided for detecting the presence or absence of silver ions in a sample. The method includes measuring one or more electrical properties of a channel along at least a portion of the length of the channel, the channel having a length and a width, the length substantially greater than the width; determining a reference channel electrical property value based on the one or more electrical properties of the channel measured during the previous measuring step; introducing a sample into the channel; measuring the one or more electrical properties of the channel along the same portion of the length of the channel that was measured in the first measuring step with the sample in the channel; determining a sample channel electrical property value based on the one or more electrical properties of the channel measured with the sample in the channel; determining any differences between the sample channel electrical property value and the reference channel electrical property value; and determining whether silver ions are present in the channel based on the differences, if any, between the sample channel electrical property value and the reference channel electrical property value.

In accordance with another exemplary embodiment, a method is provided for detecting the presence or absence of silver ions in a sample. The method includes introducing a sample and TPEA2 molecules into a channel, the channel having a length and a width, the length substantially greater than the width; measuring an electrical property value along at least a portion of the length of the channel after the sample and the TPEA2 molecules are introduced into the channel; accessing a reference electrical property value from memory, the reference electrical property value associated with at least a portion of the length of the channel; determining any differences between the measured electrical property value and the reference electrical property value; and determining whether silver ions are present in the channel based on the differences, if any, between the measured electrical property value and the reference electrical property value.

In accordance with another exemplary embodiment, a method is provided for detecting the presence or absence of silver ions in a sample. The method includes introducing TPEA2 molecules into a channel, the channel having a length and a width, the length being substantially greater than the width; measuring one or more electrical properties of the channel along at least a portion of the length of the channel; determining a reference channel electrical property value based on the one or more electrical properties of the channel measured during the previous measuring step; introducing a sample into the channel; measuring the one or more electrical properties of the channel along at least the portion of the length of the channel after the sample and the TPEA2 molecules are introduced into the channel; determining an electrical property value based on the one or more electrical properties measured after the TPEA2 molecules and the sample are introduced into the channel; determining any differences between the reference channel electrical property value and the electrical property value; and determining whether silver ions are present in the channel based on the differences, if any, between the reference channel electrical property value and the electrical property value.

In accordance with another exemplary embodiment, a method is provided for detecting the presence or absence of silver ions in a sample. The method includes introducing TPEA2 molecules into a channel, the channel having a length and a width, the length being substantially greater than the width; introducing a sample into the channel; measuring one or more electrical properties of the channel along at least a portion of the length of the channel after the sample and the TPEA2 molecules are introduced into the channel; determining an electrical property value based on the one or more electrical properties measured after the TPEA2 molecules and the sample are introduced into the channel; accessing a reference channel electrical property value, the reference channel electrical property value measured prior to introduction of both the TPEA2 molecules and the sample into the channel; determining any differences between the reference channel electrical property value and the electrical property value; and determining whether silver ions are present in the channel based on the differences, if any, between the reference channel electrical property value and the electrical property value.

In accordance with another exemplary embodiment, a method is provided for detecting the presence or absence of silver ions in a sample. The method includes introducing a sample into the channel, the channel having a length and a width, the length being substantially greater than the width; measuring one or more electrical properties of the channel along at least a portion of the length of the channel; determining a reference channel electrical property value based on the one or more electrical properties of the channel measured during the previous measuring step; introducing TPEA2 molecules into a channel; measuring the one or more electrical properties of the channel along at least the portion of the length of the channel after the sample and the TPEA2 molecules are introduced into the channel; determining an electrical property value based on the one or more electrical properties measured after the TPEA2 molecules and the sample are introduced into the channel; determining any differences between the reference channel electrical property value and the electrical property value; and determining whether silver ions are present in the channel based on the differences, if any, between the reference channel electrical property value and the electrical property value.

In accordance with another exemplary embodiment, a method is provided for detecting the presence or absence of silver ions in a sample. The method includes introducing a sample into the channel, the channel having a length and a width, the length being substantially greater than the width; introducing TPEA2 molecules into a channel; measuring one or more electrical properties of the channel along at least a portion of the length of the channel after the sample and the TPEA2 molecules are introduced into the channel; determining an electrical property value based on the one or more electrical properties measured after the TPEA2 molecules and the sample are introduced into the channel; accessing a reference channel electrical property value, the reference channel electrical property value measured prior to introduction of both the TPEA2 molecules and the sample into the channel; determining any differences between the reference channel electrical property value and the electrical property value; and determining whether silver ions are present in the channel based on the differences, if any, between the reference channel electrical property value and the electrical property value.

In accordance with another exemplary embodiment, a method is provided for detecting the presence or absence of silver ions in a sample. The method includes coating at least a portion of an inner surface of a channel with TPEA2 molecules, the channel having a length and a width, the length substantially greater than the width; measuring one or more electrical properties of the channel along at least a portion of the length of the channel after the channel is coated with the TPEA2 molecules; determining a reference channel electrical property value based on the one or more electrical properties of the channel measured during the previous measuring step; and storing the reference channel electrical property value for use in determining whether or not silver ions are present in a sample introduced in the channel.

In accordance with another exemplary embodiment, a method is provided for detecting the presence or absence of silver ions in a sample. The method includes introducing a sample and TPEA2 molecules into a channel, the channel having a length and a width, the length substantially greater than the width. The method also includes applying a first potential difference across the length of the channel in a first direction along the length of the channel. The method also includes measuring a first electrical property value of an electrical property along at least a portion of the length of the channel while the first potential difference is applied. The method also includes applying a second potential difference across the length of the channel in a second direction along the length of the channel, the second direction opposite to the first direction. The method also includes measuring a second electrical property value of the electrical property along at least the portion of the length of the channel while the second potential difference is applied. The method also includes comparing the first and second electrical property values. The method also includes determining whether silver ions are present in the channel based on the comparison between the first and second electrical property values.

In accordance with another exemplary embodiment, a silver detection system is provided. The system includes a substrate, the substrate having at least one channel, the at least one channel having a length and a width, the length substantially greater than the width; a first port in fluid communication with a first end section of the at least one channel; and a second port in fluid communication with a second end section of the at least one channel. The system also includes a first electrode electrically connected at the first end section of the at least one channel and a second electrode electrically connected at the second end section of the at least one channel, the first and second electrodes electrically connected to their respective first and second end sections of the at least one channel to form a channel circuit, the channel circuit having electrical properties and configured such that when an electrically conductive fluid is present in the at least one channel, the electrically conductive fluid alters the electrical properties of the channel circuit. The system further includes a silver detection circuit in electrical communication with the first and second electrodes, the silver detection circuit including a measurement circuit in electrical communication with the first and second electrode, the measurement circuit having a measurement circuit output, the measurement circuit output including one or more values indicative of one or more electrical properties of the channel circuit, the silver detection circuit including a memory in electrical communication with the measurement circuit output and configured to store the one or more values indicative of the one or more electrical properties of the channel circuit including at least a first value of an electrical property of the channel circuit and a second value of the electrical property of the channel circuit, the silver detection circuit further including a comparison circuit in electrical communication with the memory and having as inputs the at least first and second values, the comparison circuit configured to provide a comparison circuit output based at least in part on the at least first and/or second values, the comparison circuit output indicative of whether an silver is present in the at least one channel.

In accordance with another exemplary embodiment, a silver detection system is provided. The system includes means for accommodating a fluid flow; means for introducing a fluid at a first terminal end of the means for accommodating the fluid flow; means for outputting the fluid at a second terminal end of the means for accommodating the fluid flow; means for detecting first and second values of an electrical property of the fluid between the first and second terminal ends of the means for accommodating the fluid flow; and means for determining whether silver is present in the fluid based on a difference between the first and second values of the electrical property.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings.

Figure 1A:
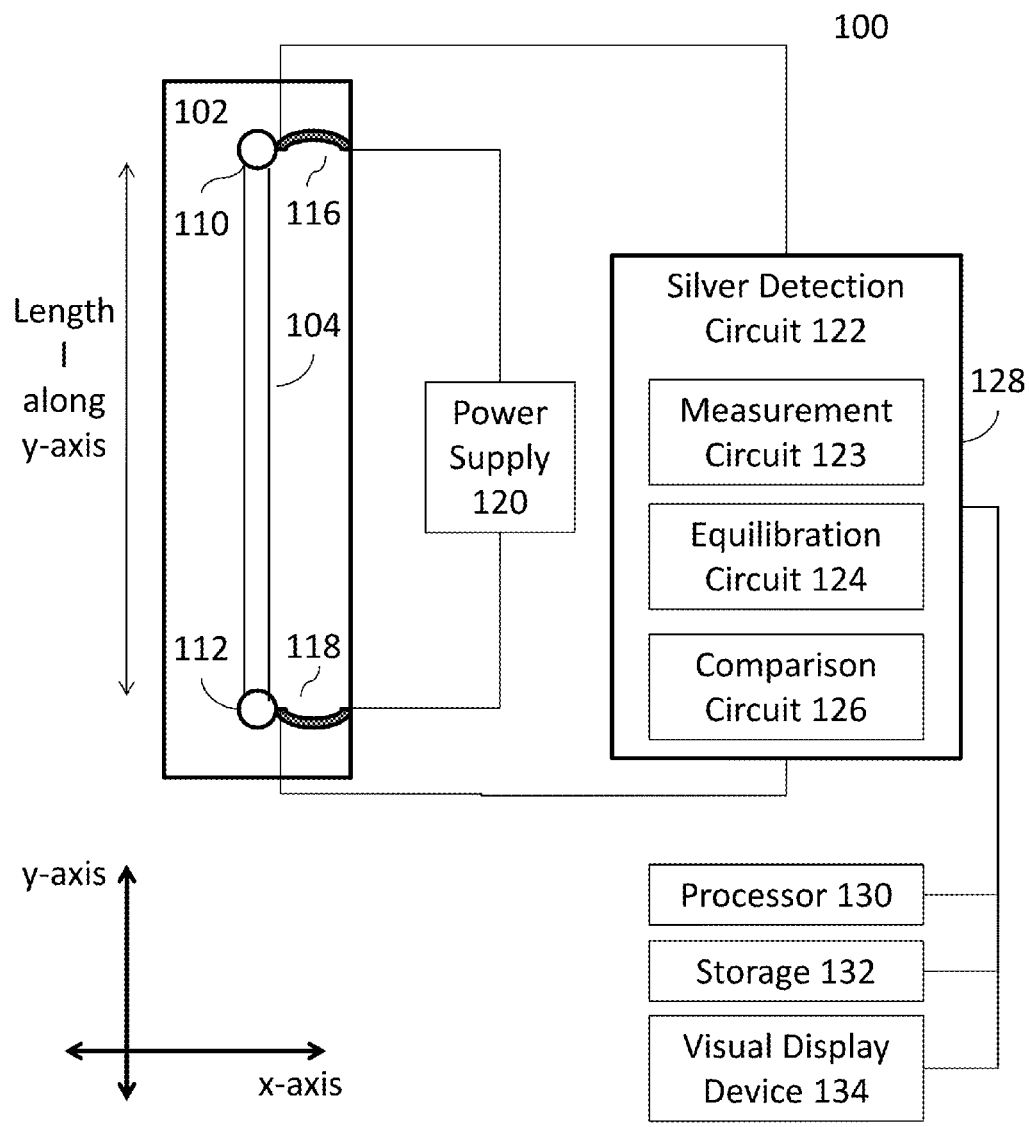
FIG. 1A illustrates a top view of an exemplary silver detection system including a single channel.

The accompanying drawings are not intended to be drawn to scale.

DETAILED DESCRIPTION

Areas for improving conventional systems and techniques of silver detection have been identified and technical solutions have been implemented in exemplary embodiments. Exemplary embodiments provide silver detection systems and techniques that couple knowledge of nano and microfluidic surface chemistry, electrokinetics and fluid dynamics to provide novel functional capabilities. Compared to conventional techniques such as nanopore technology, embodiments provide improved dimensional precision and control, resulting in new functionality and enhanced device performance.

Embodiments provide silver detection systems and methods for detecting the presence or absence of silver ions in one or more samples. An exemplary detection system includes at least one channel for accommodating a sample and a sensor compound (e.g., TPEA2), the channel having a width and a length that is significantly greater in dimension than the width. An exemplary detection system includes a silver detection circuit programmed or configured to detect one or more electrical properties along at least a portion of the length of the channel to determine whether the channel contains silver ions.

In some cases, the sensor compound (e.g., TPEA2) may be selected such that direct or indirect interaction between particles or ions of silver (if present in the sample) and particles of the sensor compound results in formation of an aggregate that alters one or more electrical properties of the channel. In certain cases, an exemplary channel may be configured to have a depth and/or a width that is substantially equal to or smaller than the diameter of a particle of the aggregate formed in the channel due to interaction between particles or ions of silver and particles of a sensor compound (e.g., TPEA2) used to detect silver ions. As such, formation of the aggregate may cause a partial or complete blockage in the flow of conductive particles in the channel, thereby decreasing the electrical current and electrical conductivity along the length of the channel and increasing the resistivity along the length of the channel. A silver detection circuit may compare this measurable change in the electrical properties of the channel upon introduction of both the sample and the sensor compound, relative to a reference value, to determine if the aggregate is present in the channel. Based on a determination that the aggregate is present in the channel, the silver detection circuit may determine that the sample contains silver ions.

In certain other cases, the aggregate particles may be electrically conductive, and formation of the aggregate particles may enhance an electrical pathway along at least a portion of the length of the channel, thereby causing a measurable increase in the electrical conductivity and electrical current measured along the length of the channel. In these cases, formation of the aggregate may cause a measurable decrease in the resistivity along the length of the channel. A silver detection circuit may compare this measurable change in the electrical properties of the channel upon introduction of both the sample and the sensor compound, relative to a reference value, to determine if the aggregate is present in the channel. Based on a determination that the aggregate is present in the channel, the silver detection circuit may determine that the sample contains silver ions.

Another exemplary technique for detecting silver ions may involve detection of the presence of a diode-like behavior in the channel that is caused by the formation of a silver aggregate in the channel. In the absence of an aggregate, application of a potential difference having a substantially similar magnitude (e.g., +500 V) may result in a substantially same magnitude of an electrical property (e.g., current) detected along the length of the channel regardless of the direction of application of the potential difference or electric field. If the potential difference is applied across the length of the channel in a first direction along the length of the channel (e.g., such that the positive electrode is at an input port at or near a first end of the channel and such that the negative electrode is at an output port at or near a second end of the channel), the resulting current may be substantially equal in magnitude to the resultant current if the potential difference is applied in the opposite direction (e.g., such that the positive electrode is at the output port and such that the negative electrode is at the input port).

Formation of an aggregate in the channel may cause a diode-like behavior in which reversal of the direction of the applied potential difference or electric field causes a change in the electrical property detected in the channel. The diode-like behavior causes the detected electrical current to vary in magnitude with the direction of the electric field. When the electric field or potential difference is applied in the first direction, the magnitude of the electrical current may be different in magnitude than when the potential different or electric field is applied in the opposite direction. Thus, comparison between a first electrical property value (detected when a potential difference is applied in a first direction along the channel length) and a second electrical property value (detected when a potential difference is applied in a second opposite direction along the channel length) may enable detection of an aggregate, and thereby detection of silver ions in the sample. If the first and second electrical property values are substantially equal in magnitude, then it may be determined that the sample does not contain silvers ions. On the other hand, if the first and second electrical property values are substantially unequal in magnitude, then it may be determined that the sample contains silver ions. In other words, the sum of the values of the electrical property (positive in one direction, negative in the other direction) is substantially zero in the absence of an aggregate and substantially non-zero in the presence of an aggregate.

In contrast to conventional nanopore techniques, exemplary embodiments involve detecting one or more electrical properties along the length of the channel, and not across the depth or thickness dimension of the channel. The channel of exemplary embodiments has a length that is significantly greater in dimension that its width and is not configured as an aperture, hole or pore. The exemplary channel thereby allows a sample and a sensor compound to flow along the length of the channel before the electrical properties are detected, thereby enabling improved dimensional precision and control over the electrical properties. Furthermore, exemplary embodiments are not limited to detection of nucleotides as in conventional nanopore techniques.

In certain embodiments, one or more properties of the channel other than electrical properties may be detected in determining whether silver is present in the channel. These properties may be detected using techniques that include, but are not limited to, acoustic detection, resonance-wise parametric detection, optical detection, spectroscopic detection, fluorescent dyes, and the like.

I. Definitions of Terms

Certain terms used in connection with exemplary embodiments are defined below.

As used herein, the terms "detection system," "detection method" and "detection technique" encompass systems and methods for detecting an analyte in a sample by measuring one or more electrical properties along at least a portion of a length of at least one channel. The analyte may be silver in one embodiment.

As used herein, the term "channel" encompasses a conduit in a detection system that is configured to have a well-defined inner surface and an inner space bounded by the inner surface that is configured to accommodate a fluid. In some embodiments, the inner surface of the channel is micro-fabricated and configured to present a smooth surface. An exemplary channel may have the following dimensions: a length, l, measured along its longest dimension (y-axis) and extending along a plane substantially parallel to a substrate of the detection system; a width, w, measured along an axis (x-axis) perpendicular to its longest dimension and extending substantially along the plane parallel to the substrate; and a depth, d, measured along an axis (z-axis) substantially perpendicular to the plane parallel to the substrate. An exemplary channel may have a length that is substantially greater than its width and its depth. In some cases, exemplary ratios between the length:width may include, but are not limited to, about 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, all intermediate ratios, and the like. In certain cases, an exemplary channel may be configured to have a depth and/or a width that is substantially equal to or smaller than the diameter of an aggregate particle that may be formed in the channel due to interaction between a sensor compound and an analyte of interest.

As used herein, the term "analyte" encompasses a substance whose presence or absence may be detected using an exemplary detection system or method. Exemplary analytes that may be detected using exemplary embodiments may include organic (e.g., biomolecules) or inorganic (e.g., metal ions) substances. Certain analytes that may be detected using exemplary embodiments include, but are not limited to, silver, mercury, one or more solvents, and one or more nucleic acids.

As used herein, the term "sample" encompasses a test substance that may be analyzed by an exemplary detection system or method to determine whether the sample includes an analyte of interest. Exemplary samples that may be tested in exemplary embodiments include, but are not limited to: any fluids, including those derived from biological fluids like saliva, blood, plasma, urine, stool; soil samples; municipal water samples; air samples; and the like.

As used herein, the terms "sensor" and "sensor compound" encompass a substance that interacts, directly or indirectly, with an analyte of interest in a sample to cause formation of an aggregate. In an example in which an analyte of interest is silver, a suitable sensor compound may be TPEA2.

As used herein, the term "aggregate" encompasses a macromolecular structure composed of particles of an analyte and particles of a sensor compound. As such, an aggregate particle has a unit dimension or unit size that is larger than the unit dimension or unit size of an analyte particle and that is larger than the dimension or unit size of a sensor compound. An aggregate may form in a channel of an exemplary detection system due to direct or indirect interaction between the particles of an analyte and the particles of a sensor compound. In exemplary detection systems and methods for detecting a particular analyte, a sensor compound may be selected such that the sensor compound interacts with the analyte, directly or indirectly via other substances, to result in formation of an aggregate in a channel. Presence of the aggregate particles in the channel therefore indicates presence of the analyte in the channel, whereas absence of the aggregate particles in the channel indicates absence of the analyte in the channel.

In certain cases in which a potential difference is applied across at least a portion of the length of the channel, formation of an aggregate may cause a partial or complete blockage in fluid flow in the channel and may cause a measurable decrease in an electrical conductivity or current along at least a portion of the length of the channel and/or a measurable increase in the electrical resistivity. In certain other cases, particles of an aggregate may be electrically conductive, and therefore formation of the aggregate may enhance the electrical conductivity of the channel, thereby causing a measurable increase in the electrical conductivity or current along at least a portion of the length of the channel and/or a measurable decrease in the electrical resistivity.

As used herein, the term "electrical property" encompasses one or more characteristics of a channel including, but not limited to, measures that quantify how much electric current is conducted along the channel, the ability of the channel (and/or any contents of the channel) to conduct an electric current, how strongly the channel (and/or any contents of the channel) opposes the flow of electrical current, and the like. In exemplary embodiments, an electrical property may be detected along at least a portion of the length of the channel. Exemplary electrical properties detected in embodiments include, but are not limited to, a measure of an electrical current conducted along at least a portion of the length of the channel, a measure of an electrical conductivity along at least a portion of the length of the channel, a measure of electrical resistivity along at least a portion of the length of the channel, a measure of potential difference across at least a portion of the length of a channel, combinations thereof, and the like.

As used herein, the term "reference" with respect to an electrical property value encompasses a value or range of values of an electrical property of a channel prior to a state in which both a sample and a sensor compound have been introduced into the channel and allowed to interact with each other in the channel. That is, the reference value is a value characterizing the channel prior to any interaction between an analyte of interest in the sample and the sensor compound. In some cases, the reference value may be detected at a time period after introduction of the sensor compound into the channel but before introduction of the sample into the channel. In some cases, the reference value may be detected at a time period after introduction of the sample into the channel but before introduction of the sensor compound into the channel. In some cases, the reference value may be detected at a time period before introduction of either the sample or the sensor compound into the channel. In some cases, the reference value may be detected at a time period before introduction of either the sample or the sensor compound into the channel but after introduction of a buffer solution into the channel.

In some cases, the reference value may be predetermined and stored on a non-transitory storage medium from which it may be accessed. In other cases, the reference value may be determined from one or more electrical property measurements during use of the detection system.

As used herein, the terms "data," "content," "information," and similar terms may be used interchangeably to refer to data capable of being transmitted, received, and/or stored in accordance with embodiments of the present invention. Thus, use of any such terms should not be taken to limit the spirit and scope of embodiments of the present invention. Further, where a module, processor or device is described herein to receive data from another module, processor or device, it will be appreciated that the data may be received directly from the another module, processor or device or may be received indirectly via one or more intermediary modules or devices, such as, for example, one or more servers, relays, routers, network access points, base stations, hosts, and/or the like, sometimes referred to herein as a "network." Similarly, where a computing device is described herein to send data to another computing device, it will be appreciated that the data may be sent directly to the another computing device or may be sent indirectly via one or more intermediary computing devices, such as, for example, one or more servers, relays, routers, network access points, base stations, hosts, and/or the like.

As used herein, the term "module," encompasses hardware, software and/or firmware configured to perform one or more particular functions.

As used herein, the term "computer-readable medium" refers to a non-transitory storage hardware, non-transitory storage device or non-transitory computer system memory that may be accessed by a controller, a microcontroller, a computational system or a module of a computational system to encode thereon computer-executable instructions or software programs. A "non-transitory computer-readable medium" may be accessed by a computational system or a module of a computational system to retrieve and/or execute the computer-executable instructions or software programs encoded on the medium. A non-transitory computer-readable medium may include, but is not limited to, one or more types of non-transitory hardware memory, non-transitory tangible media (for example, one or more magnetic storage disks, one or more optical disks, one or more USB flash drives), computer system memory or random access memory (such as, DRAM, SRAM, EDO RAM), and the like.

As used herein, the term "set" refers to a collection of one or more items.

As used herein, the term "plurality" refers to two or more items.

As used herein, the terms "equal" and "substantially equal" refer interchangeably, in a broad lay sense, to exact equality or approximate equality within some tolerance.

As used herein, the terms "similar" and "substantially similar" refer interchangeably, in a broad lay sense, to exact sameness or approximate similarity within some tolerance.

As used herein, the terms "couple" and "connect" encompass direct or indirect connection among two or more components. For example, a first component may be coupled to a second component directly or through one or more intermediate components.

Some exemplary embodiments of the present invention will now be described more fully hereinafter with reference to the accompanying drawings in which some, but not all, embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

II. Exemplary Silver Detection Systems

An exemplary silver detection system includes at least one channel and is configured to detect one or more electrical properties along at least a portion of the length of the channel to determine whether the channel contains silver ions. An exemplary detection system may be configured to include one or more channels for accommodating a sample and a sensor compound (e.g., TPEA2), one or more input ports for introduction of the sample and the sensor compound into the channel and, in some embodiments, one or more output ports through which the contents of the channel may be removed.

A sensor compound (e.g., TPEA2) may be selected such that direct or indirect interaction between particles of silver (if present in the sample) and particles of the sensor compound result in formation of an aggregate that alters one or more electrical properties of at least a portion of the length of the channel. In certain cases, formation of the aggregate particles may inhibit or block fluid flow in the channel, and may therefore cause a measurable drop in the electrical conductivity and electrical current measured along the length of the channel. Similarly, in these cases, formation of the aggregate may cause a measurable increase in the resistivity along the length of the channel. In certain other cases, the aggregate particles may be electrically conductive, and formation of the aggregate particles may enhance an electrical pathway along at least a portion of the length of the channel, thereby causing a measurable increase in the electrical conductivity and electrical current measured along the length of the channel. In these cases, formation of the aggregate may cause a measurable decrease in the resistivity along the length of the channel.

An exemplary channel may have the following dimensions: a length measured along its longest dimension (y-axis) and extending along a plane parallel to the substrate of the detection system; a width measured along an axis (x-axis) perpendicular to its longest dimension and extending along the plane parallel to the substrate; and a depth measured along an axis (z-axis) perpendicular to the plane parallel to the substrate. An exemplary channel may have a length that is substantially greater than its width and its depth. In some cases, exemplary ratios between the length: width may be about 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, intermediate ratios, and the like.

In certain cases, an exemplary channel may be configured to have a depth and/or a width that is substantially equal to or smaller than the diameter of a particle of an aggregate formed in the channel due to interaction between particles of silver and particles of a sensor compound (e.g., TPEA2) used to detect silver.

An exemplary channel may have a width taken along the x-axis ranging from about 1 nm to about 50,000 nm, but is not limited to this exemplary range. An exemplary channel may have a length taken along the y-axis ranging from about 10 nm to about 2 cm, but is not limited to this exemplary range. An exemplary channel may have a depth taken along the z-axis ranging from about 1 nm to about 1 micron, but is not limited to this exemplary range.

An exemplary channel may have any suitable transverse cross-sectional shape (i.e., a cross-section taken along the x-z plane) including, but not limited to, circular, elliptical, rectangular, square, D-shaped (due to isotropic etching), and the like.

Figure 1B:
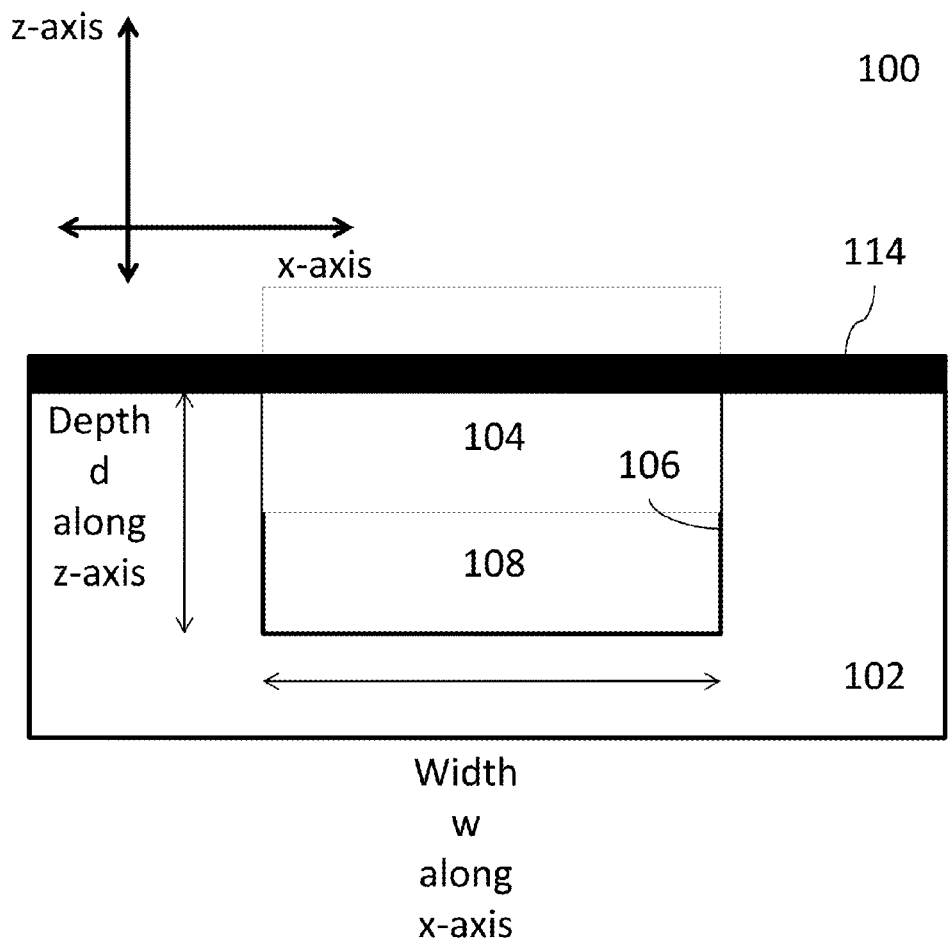
FIG. 1B illustrates a cross-sectional side view of the exemplary silver detection system of FIG. 1A.

FIGS. 1A and 1B illustrate an exemplary detection system 100 that may be used to detect presence or absence of silver in a sample. FIG. 1A is a top view of the system, while FIG. 1B is a cross-sectional side view of the system. The detection system 100 includes a substrate 102 that extends substantially along a horizontal x-y plane. In some embodiments, the substrate 102 may be formed of a dielectric material, for example, silica. Other exemplary materials for the substrate 102 include, but are not limited to, glass, sapphire, diamond, and the like.

The substrate 102 may support or include a channel 104 having at least an inner surface 106 and an inner space 108 for accommodating a fluid. In some cases, the channel 104 may be etched in a top surface of the substrate 102. Exemplary materials for the inner surfaces 106 of the channel 104 include, but are not limited to, glass, silica, and the like.

The channel 104 and the substrate 102 may be formed of glass in certain embodiments. Biological conditions represent a barrier to the use of glass-derived implantations due to the slow dissolution of glass into biological fluids and adhesion of proteins and small molecules to the glass surface. In certain non-limiting embodiments, surface modification using a self-assembled monolayer offers an approach for modifying glass surfaces for silver detection and analysis. In certain embodiments, at least a portion of the inner surface 106 of the channel 104 may be pre-treated or covalently modified to include or be coated with a material that enables specific covalent binding of a sensor compound to the inner surface. In certain embodiments, a cover slip 114 covering the channel may also be covalently modified with a material.

Exemplary materials that may be used to modify the inner surface 106 of the channel 104 include, but are not limited to, a silane compound (e.g., tricholorsilane, alkylsilane, triethoxysilane, perfluoro silane), zwitterionic sultone, poly (6-9)ethylene glycol (Peg), perfluorooctyl, fluorescein, an aldehyde, a graphene compound, and the like. The covalent modification of the inner surface of the channel may prevent non-specific absorption of certain molecules. In one example, covalent modification of the inner surface may enable covalent bonding of sensor compound molecules to the inner surface while preventing non-specific absorption of other molecules to the inner surface. For example, poly (ethylene glycol) (Peg) may be used to modify the inner surface 106 of the channel 104 to reduce non-specific adsorption of materials to the inner surface.

In some embodiments, the channel 104 may be nano or micro-fabricated to have a well-defined and smooth inner surface 106. Exemplary techniques for fabricating a channel and modifying the inner surface of a channel are taught in Sumita Pennathur and Pete Crisalli (2014), "Low Temperature Fabrication and Surface Modification Methods for Fused Silica Micro- and Nanochannels," MRS Proceedings, 1659, pp 15-26. doi:10.1557/op1.2014.32, the entire contents of which are expressly incorporated herein by reference.

A first end section of the channel 104 may include or be in fluid communication with an input port 110, and a second end section of the channel 104 may include or be in fluid communication with an output port 112. In certain non-limiting embodiments, the ports 110 and 112 may be provided at terminal ends of the channel 104.

The top surface of the substrate 102 having the channel 104 and the ports 110, 112 may be covered and sealed with a cover slip 114 in some embodiments.

A first electrode 116 may be electrically connected at the first end section of the channel 104, for example, at or near the input port 110. A second electrode 118 may be electrically connected at the second end section of the channel 104, for example, at or near the output port 112. The first and second electrodes 116, 118 may be electrically connected to a power supply or voltage source 120 in order to apply a potential difference between the first and second electrodes. That is, the potential difference is applied across at least a portion of the length of the channel. When a fluid is present in the channel 104 and is under the influence of the applied potential difference, the electrodes 116, 118 and the fluid may create a complete electrical pathway.

The power supply or voltage source 120 may be configured to apply an electric field in a reversible manner such that a potential difference is applied in a first direction along the channel length (along the y-axis) and also in a second opposite direction (along the y-axis). In one example in which the electric field or potential difference direction is in a first direction, the positive electrode may be connected at the first end section of the channel 104, for example, at or near the input port 110, and the negative electrode may be connected at the second end section of the channel 104, for example, at or near the output port 112. In another example in which the electric field or potential difference direction is in a second opposite direction, the negative electrode may be connected at the first end section of the channel 104, for example, at or near the input port 110, and the positive electrode may be connected at the second end section of the channel 104, for example, at or near the output port 112.

The first and second end sections of the channel 104 (i.e., at or near the input port 110 and the output port 112) may be electrically connected to a silver detection circuit 122 that is programmed or configured to detect values of one or more electrical properties of the channel 104 for determining whether silver ions are present or absent in the channel 104. The electrical property values may be detected at a single time period (for example, a certain time period after introduction of both a sample and a sensor compound into the channel), or at multiple different time periods (for example, before and after introduction of both the sample and the sensor compound into the channel). Exemplary electrical properties detected may include, but are not limited to, electrical current, conductivity voltage, resistance, and the like. Certain exemplary silver detection circuits 122 may include or be configured as a processor or a computing device, for example as device 1600 illustrated in FIG. 17. Certain other silver detection circuits 122 may include, but are not limited to, an ammeter, a voltmeter, an ohmmeter, and the like.

In one embodiment, the silver detection circuit 122 may include a measurement circuit 123 programmed or configured to measure one or more electrical property values along at least a portion of a length of the channel 104. The silver detection circuit 122 may also include an equilibration circuit 124 that is programmed or configured to periodically or continually monitor one or more values of an electrical property of the channel over a time period, and to select a single one of the values after the values have reached equilibrium (i.e., have stopped varying beyond a certain threshold of variance or tolerance).

The silver detection circuit 122 may also include a comparison circuit 126 that is programmed or configured to compare two or more electrical property values of the channel, for example, a reference electrical property value (measured before a state in which both the sample and the sensor compound have been introduced into the channel) and an electrical property value (measured after introduction of both the sample and the sensor compound into the channel). The comparison circuit 126 may use the comparison in order to determine whether silver is present or absent in the channel. In one embodiment, the comparison circuit 126 may calculate a difference between the measured electrical property value and the reference electrical property value, and compare the difference to a predetermined value indicative of the presence or absence of silver in the channel.

In certain embodiments, upon introduction of both the sample and the sensor compound into the channel, the comparison circuit 126 may be programmed or configured to compare a first electrical property value (e.g., magnitude of electrical current) when the electric field or potential difference is applied across the channel in a first direction along the length of the channel to a second electrical property value (e.g., magnitude of electrical current) when the electric field or potential difference is applied across the channel in a second opposite direction along the length of the channel. In one embodiment, the comparison circuit 126 may calculate a difference between the magnitudes of the first and second values, and compare the difference to a predetermined value (e.g., whether the difference is substantially zero) indicative of the presence or absence of silver in the channel. For example, if the difference is substantially zero, this indicates absence of a silver aggregate in the channel, i.e., absence of silver ions in the channel. If the difference is substantially non-zero, this indicates presence of a silver aggregate in the channel, i.e., presence of silver ions in the channel.

In certain embodiments, the silver detection circuit 122 may be programmed or configured to determine an absolute concentration of silver ions in a sample, and/or a relative concentration of silver ions relative to one or more additional substances in a sample.

In some embodiments, the comparison circuit 124 and the equilibration circuit 126 may be configured as separate circuits or modules; while in other embodiments, they may be configured as a single integrated circuit or module.

The silver detection circuit 122 may have an output 128 that may, in some embodiments, be connected to one or more external devices or modules. For example, the silver detection circuit 122 may transmit a reference electrical property value and/or one or more measured electrical property values to one or more of: a processor 130 for further computation, processing and analysis, a non-transitory storage device or memory 132 for storage of the values, and a visual display device 134 for display of the values to a user. In some cases, the silver detection circuit 122 may itself generate an indication of whether the sample includes silver ions, and may transmit this indication to the processor 130, the non-transitory storage device or memory 132 and/or the visual display device 134.

In an exemplary method of using the system of FIGS. 1A and 1B, a sensor compound (e.g., TPEA2) and a sample may be sequentially or concurrently introduced into the channel.

When flow of the fluid and/or flow of the charged particles in the fluid is uninhibited (for example, due to absence of an aggregate), the conductive particles or ions in the fluid may travel along at least a portion of the length of the channel 104 along the y-axis from the input port 110 toward the output port 112. The movement of the conductive particles or ions may result in a first or "reference" electrical property value or range of values (e.g., of an electrical current, conductivity, resistivity) being detected by the silver detection circuit 122 along at least a portion of the length of the channel 104. In some embodiments, the equilibration circuit 124 may periodically or continually monitor electrical property values during a time period until the values reach equilibrium. The equilibration circuit 124 may then select one of the values as the reference electrical property value to avoid the influence of transient changes in the electrical property.

The term "reference" electrical property value may refer to a value or range of values of an electrical property of a channel prior to introduction of both a sample and a sensor compound (e.g., TPEA2) in the channel. That is, the reference value is a value characterizing the channel prior to any interaction between silver in the sample and the sensor compound. In some cases, the reference value may be detected at a time period after introduction of the sensor compound into the channel but before introduction of the sample into the channel. In some cases, the reference value may be detected at a time period after introduction of the sample into the channel but before introduction of the sensor compound into the channel. In some cases, the reference value may be detected at a time period before introduction of either the sample or the sensor compound into the channel. In some cases, the reference value may be predetermined and stored on a non-transitory storage medium from which it may be accessed.

However, when flow of the fluid and/or flow of the charged particles in the fluid is partially or completely blocked (for example, by formation of an aggregate), the conductive particles or ions in the fluid may be unable to freely travel along at least a portion of the length of the channel 104 along the y-axis from the input port 110 toward the output port 112. The hindered or stopped movement of the conductive particles or ions may result in a second electrical property value or range of values (e.g., of an electrical current, conductivity, resistivity) being detected by the silver detection circuit 122 along at least a portion of the length of the channel 104. In some embodiments, the silver detection circuit 122 may wait for a waiting or adjustment time period after introduction of both the sample and the sensor compound into the channel prior to detecting the second electrical property value. The waiting or adjustment time period allows an aggregate to form in the channel and for the aggregate formation to alter the electrical properties of the channel.

In some embodiments, the equilibration circuit 124 may periodically or continually monitor electrical property values during a time period after the introduction of both the sample and the sensor compound until the values reach equilibrium. The equilibration circuit 124 may then select one of the values as the second electrical property value to avoid the influence of transient changes in the electrical property.

The comparison circuit 126 may compare the second electrical property value to the reference electrical property value. If it is determined that the difference between the second value and the reference value corresponds to a predetermined range of decrease in current or conductivity (or increase in resistivity), the silver detection circuit 122 may determine that a silver aggregate is present in the channel and that, therefore, silver ions are present in the sample.

Figure 2:
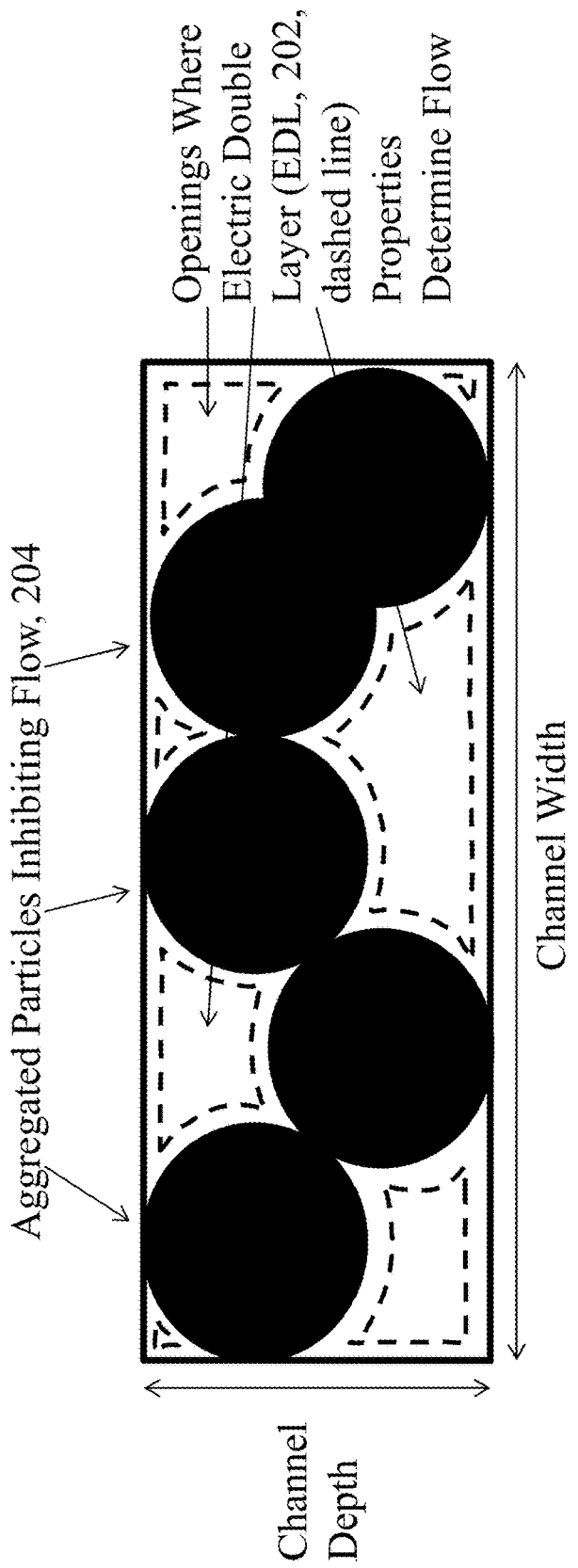
FIG. 2 illustrates a schematic cross-sectional side view of the channel of the exemplary silver detection system of FIG. 1A, showing aggregate particles and an electrical double layer (EDL).

The fluid flow along the length of the channel may depend on the size of the aggregate particles in relation to the dimensions of the channel, and the formation of an electrical double layer (EDL) at the inner surface of the channel. FIG. 2 illustrates a cross-sectional side view of an exemplary channel of the detection system of FIGS. 1A and 1B, in which the combination of an electric double layer (EDL) 202 at the inner surface of the channel and aggregate particles 204 is shown to inhibit fluid flow in the channel.

In general terms, an EDL is a region of net charge between a charged solid (e.g., the inner surface of the channel, a silver particle, an aggregate particle) and an electrolyte-containing solution (e.g., the fluid contents of the channel). EDLs exist around both the inner surface of the channel and around any silver particles and aggregate particles within the channel. The counter-ions from the electrolyte are attracted towards the charge of the inner surface of the channel, and induce a region of net charge. The EDL affects ion flow within the channel and around silver particles and aggregate particles of interest, creating a diode-like behavior by not allowing any of the counter-ions to pass through the length of the channel.

To mathematically solve for the characteristic length of the EDL, the Poisson-Boltzmann (PB) equation and/or Poisson-Nernst-Plank equations (PNP) may be solved. These solutions are coupled to the Navier-Stokes (NS) equations for fluid flow to create a nonlinear set of coupled equations that are analyzed to understand the operation of the exemplary system.

In view of the dimensional interplay among the channel surface, the EDLs and the aggregate particles, exemplary channels may be configured and constructed with carefully selected dimensional parameters that ensure that flow of conductive ions is substantially inhibited along the length of the channel when an aggregate of a certain predetermined size is formed in the channel. In certain cases, an exemplary channel may be configured to have a depth and/or a width that is substantially equal to or smaller than the diameter of an aggregate particle formed in the channel during silver detection. In certain embodiments, the sizes of the EDLs may also be taken into account in selecting dimensional parameters for the channel. In certain cases, an exemplary channel may be configured to have a depth and/or a width that is substantially equal to or smaller than the dimension of the EDL generated around the inner surface of the channel and the aggregate particles in the channel.

In some cases, formation of an electrically conductive aggregate may enhance the electrical pathway along at least a portion of the length of the channel 104. In this case, the silver detection circuit 122 may detect a third electrical property value or range of values (e.g., of an electrical current, conductivity, resistivity) along at least a portion of the length of the channel 104. In some embodiments, the silver detection circuit 122 may wait for a waiting or adjustment time period after introduction of both the sample and the sensor compound into the channel prior to detecting the third electrical property value. The waiting or adjustment time period allows an aggregate to form in the channel and for the aggregate formation to alter the electrical properties of the channel.

In some embodiments, the equilibration circuit 124 may periodically or continually monitor electrical property values during a time period after the introduction of both the sample and the sensor compound until the values reach equilibrium. The equilibration circuit 124 may then select one of the values as the third electrical property value to avoid the influence of transient changes in the electrical property.

The comparison circuit 126 may compare the third electrical property value to the reference electrical property value. If it is determined that the difference between the third value and the reference value corresponds to a predetermined range of increase in current or conductivity (or decrease in resistivity), the silver detection circuit 122 may determine that a silver aggregate is present in the channel and that, therefore, silver ions are present in the sample.

In certain embodiments, prior to use of the detection system, the channel may be free of the sensor compound (e.g., TPEA2). That is, a manufacturer of the detection system may not pre-treat or modify the channel to include the sensor compound. In this case, during use, a user may introduce the sensor compound, for example in an electrolyte buffer, into the channel and detect a reference electrical property value of the channel with the sensor compound but in the absence of a sample.

In certain other embodiments, prior to use of the detection system, the channel may be pre-treated or modified so that at least a portion of an inner surface of the channel includes or is coated with the sensor compound (e.g., TPEA2). That is, a manufacturer of the detection system may pre-treat or modify the channel to include the sensor compound. In this case, a user may only need to introduce the sample into the channel. In one example, the manufacturer may detect a reference electrical property value of the channel with the sensor compound and, during use, a user may access the stored reference electrical property value.

Certain exemplary detection systems may include a single channel. Certain other exemplary detection systems may include multiple channels provided on a single substrate. Such detection systems may include any suitable number of channels including, but not limited to, 2, 3, 4, 5, 6, 7, 8, 9, 10, and the like.

In one embodiment, a detection system may include a plurality of channels in which at least two channels operate independent of each other. The exemplary channel 104 and associated components of FIGS. 1A and 1B may be reproduced on the same substrate to achieve such a multi-channel detection system. The multiple channels may be used to detect silver ions in the same sample, different analytes in the same sample, silver ions in different samples, and/or different analytes in different samples.

Figure 3:
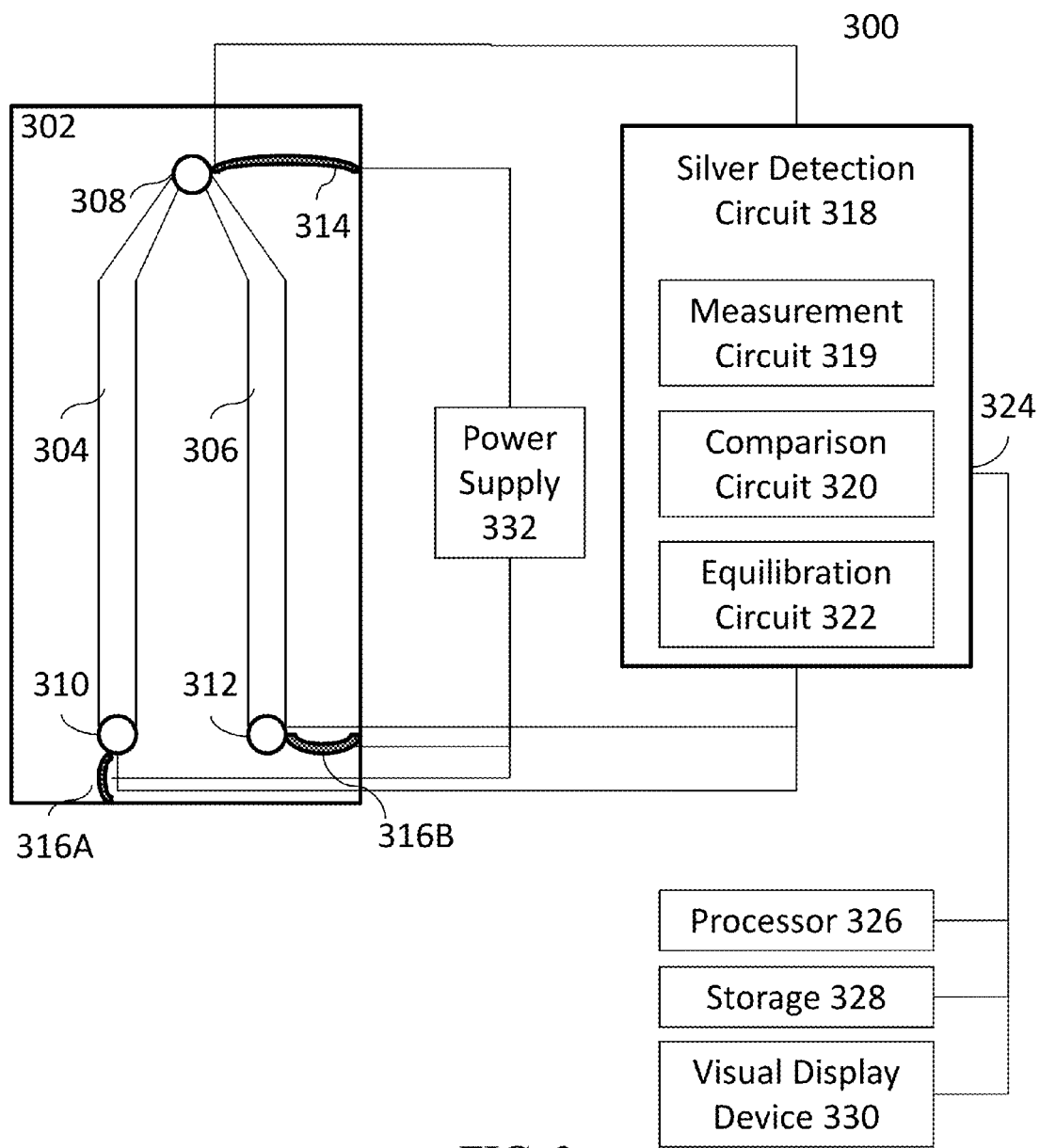
FIG. 3 illustrates a top view of an exemplary silver detection system including multiple channels.

In another embodiment, a detection system may include a plurality of channels in which at least two channels operate in cooperation with each other. FIG. 3 illustrates an exemplary detection system 300 including a substrate 302. The substrate 302 may include a plurality of channels 304, 306 that may be used to detect silver ions in the same sample. Although two channels are represented, more channels may be provided in the detection system. The provision of multiple channels may allow redundancy and error-checking functionalities, whereby different silver detection results in the channels may indicate that the detection system is not performing reliably and whereby the same result in the channels may indicate that the detection system is performing reliably. In the former case, the detection system may need to be repaired, recalibrated or discarded.

First end sections of the first channel 304 and the second channel 306 may include or be in fluid communication with a common input port 308 at which a sample and a sensor compound may be introduced into the detection system. A second end section of the first channel 304 may include or be in fluid communication with a first output port 310, and a second end section of the second channel 306 may include or be in fluid communication with a second output port 312. The output ports 310 and 312 may not be in fluid communication with each other.

The detection system 300 may include electrodes 314, 316A and 316B that may be electrically connected at or near the end sections of the first and second channels 304, 306. The electrodes 314, 316A and 316B may connect the channels 304, 306 to a voltage or power supply 332 in order to apply a potential difference across the input port 308 and the first output port 310 and across the input port 308 and the second output port 312. Similarly, a silver detection circuit 318 may be electrically connected at or near the end sections of the first and second channels 304, 306 to determine whether the sample introduced into both channels contain silver ions.

Components represented in FIG. 3 that are in common with components represented in FIGS. 1A and 1B are described in connection with FIGS. 1A and 1B.

Figure 4:
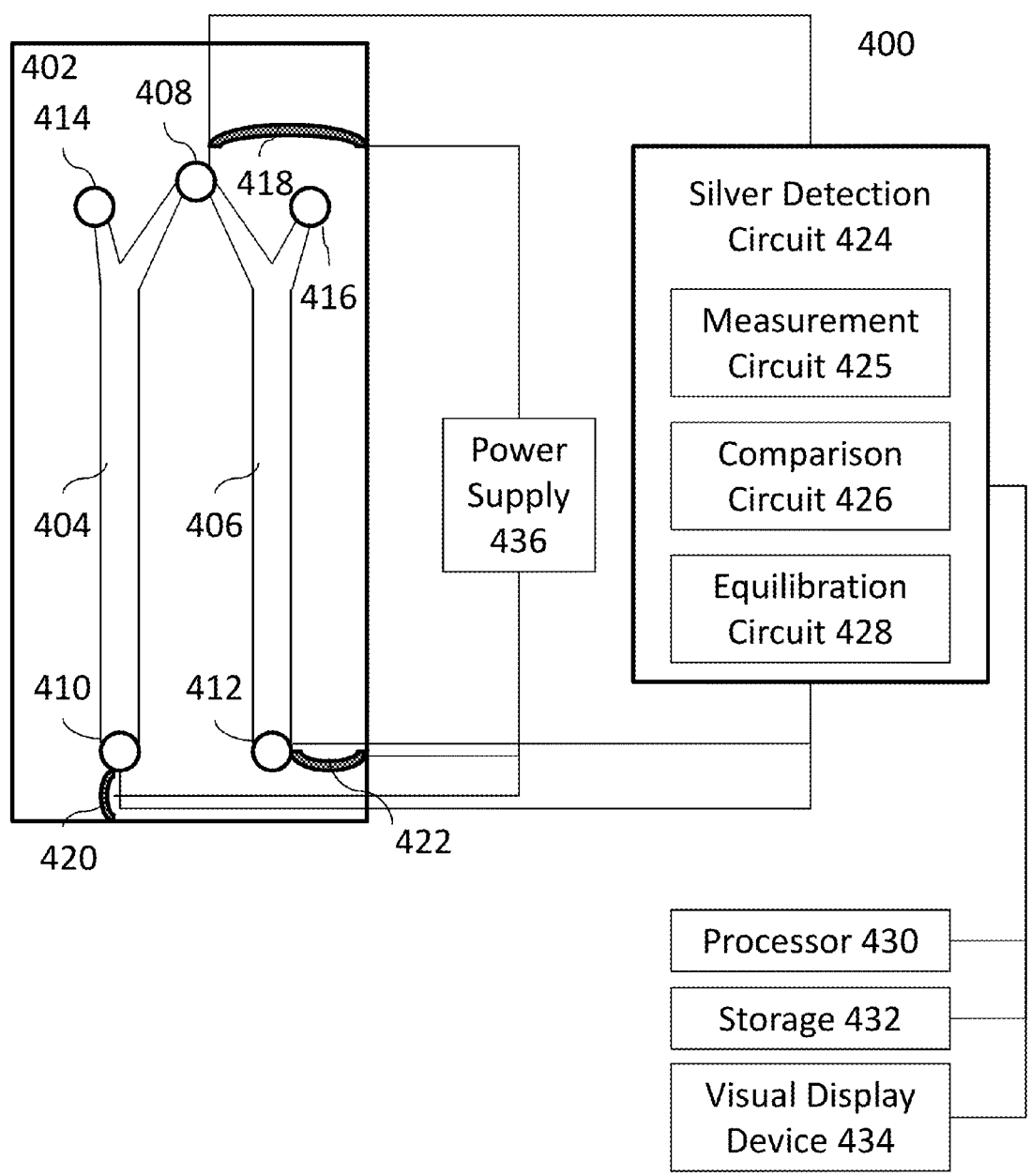
FIG. 4 illustrates a top view of another exemplary silver detection system including multiple channels.

In another embodiment, a detection system may include a plurality of channels in which at least two channels operate in cooperation with each other. FIG. 4 illustrates an exemplary detection system 400 including a substrate 402. The substrate 402 may include a plurality of channels 404, 406 that may be used to detect silver in different samples or different analytes in the same sample. Although two channels are represented, more channels may be provided in the detection system. The provision of multiple channels may allow concurrent detection of multiple analytes in the same sample or silver ions in multiple samples, thereby improving the speed and throughput of the detection system.

First end sections of the first channel 404 and the second channel 406 may include or be in fluid communication with a common first input port 408 at which a sample or a sensor compound may be introduced into the detection system. In addition, the first end section of the first channel 404 may include or be in fluid communication with a second input port 414. The first end section of the second channel 406 may include or be in fluid communication with a third input port 416. The second and third input ports 414, 416 may not be in fluid communication with other.

A second end section of the first channel 404 may include or be in fluid communication with a first output port 410, and a second end section of the second channel 406 may include or be in fluid communication with a second output port 412. The output ports 410 and 412 may not be in fluid communication with each other.

The detection system 400 may include electrodes 418, 420 and 422 that may be electrically connected at or near the end sections of the first and second channels 404, 406. The electrodes may electrically connect the first and second channels to a voltage or power source 436 in order to apply a potential difference across the first input port 408 and the first output port 410 and across the first input port 408 and the second output port 412. Similarly, a silver detection circuit 424 may be electrically connected at or near the end sections of the first and second channels 404, 406 to determine whether one or more samples introduced into the channels contain silver.

Components represented in FIG. 4 that are in common with components represented in FIGS. 1A and 1B are described in connection with FIGS. 1A and 1B.

In an exemplary method of using the system 400 of FIG. 4, a sample may be introduced into the common first input port 408, and first and second sensor compounds may be introduced at the second and third input ports 414 and 416, respectively. As a result, based on measurements taken at the first and second end sections of the first channel 404, the silver detection circuit 424 may determine whether the sample includes a first analyte of interest (which interacts with the first sensor compound in the first channel to form an aggregate). Based on measurements taken at the first and second end sections of the second channel 406, the silver detection circuit 424 may determine whether the sample includes a second analyte of interest (which interacts with the second sensor compound in the second channel to form an aggregate).

In another exemplary method of use, a sensor compound may be introduced into the common first input port 408, and first and second samples may be introduced at the second and third input ports 414 and 416, respectively. As a result, based on measurements taken at the first and second end sections of the first channel 404, the silver detection circuit 424 may determine whether the first sample includes silver ions (which interact with the sensor compound in the first channel to form an aggregate). Based on measurements taken at the first and second end sections of the second channel 406, the silver detection circuit may 424 determine whether the second sample includes silver ions (which interact with the sensor compound in the second channel to form an aggregate).

In certain embodiments, the systems illustrated in FIGS. 1-4 may be used to determine an absolute or relative concentration of silver ions based on one or more electrical property values of the channel. The concentration of silver ions may be determined in such a manner because the channels of exemplary detection systems have a high inner surface area to volume ratio. At low concentrations of silver ions, electrical conductivity in the channel is dominated by surface charges. As such, measurements of electrical properties of the channel can enable distinction between different ions. As a result, unique and sensitive measurements of the bulk flow in the channel can be used to determine information on the surface charges at the inner surface of the channel. Exemplary embodiments may thus compute predetermined ranges of electrical property values of the channel that are characteristic of silver ions given the dimensions of the channel and at different concentrations of silver ions. These predetermined values may then be used to determine an unknown concentration of silver ions in a sample.

Detailed information on surface charges in the channel for different ions is presented in the following papers, the entire contents of which are expressly incorporated herein by reference: "Surface-dependent chemical equilibrium constants and capacitances for bare and 3-cyanopropyldimethylchlorosilane coated silica nanochannels," M. B. Andersen, J. Frey, S. Pennathur and H. Bruus, J. Colloid Interface Sci. 353, 301-310 (2011), and "Hydronium-domination ion transport in carbon-dioxide-saturated electrolytes at low salt concentrations in nanochannels," K. L. Jensen, J. T. Kristensen, A. M. Crumrine, M. B. Andersen, H. Bruus and S. Pennathur, Phys. Review E. 83, 5, 056307.

Figure 5:
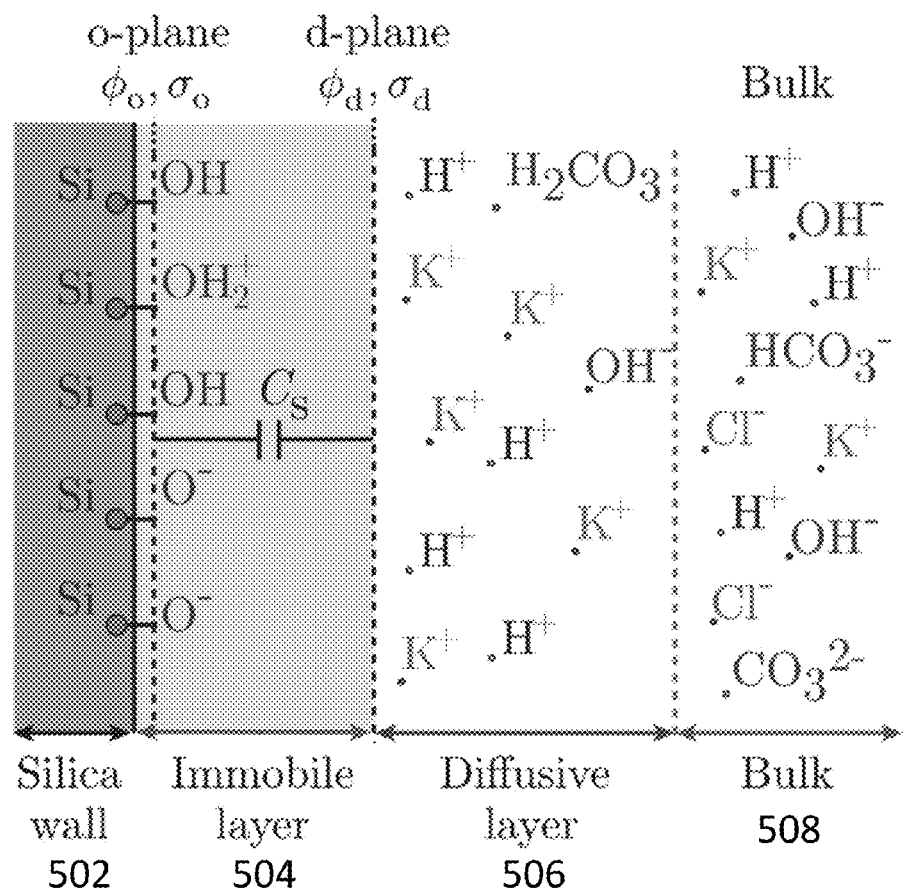
FIG. 5 is a schematic representing exemplary ions in an exemplary detection system.

FIG. 5 is a schematic drawing of the inside of a channel including an inner surface of the channel 502, an immobile layer of fluid 504 lying immediately adjacent to the inner surface of the channel, a diffusive layer of fluid 506 lying immediately adjacent to the immobile layer, and a bulk fluid flow layer 508 lying immediately adjacent to the diffusive layer. Exemplary ions are represented in each of the fluid layers. Upon application of a potential difference across the length of the channel, an electrical property value may be detected along at least a portion of the length of the channel (for example, by the silver detection circuit 122). The comparison circuit 126 may be used to compare the measured electrical property value to a predetermined range of electrical property values that correspond to a particular concentration or range of concentration values of silver ions. The concentration determined may be an absolute concentration of silver ions or a relative concentration of silver ions with respect to the concentrations of one or more other substances in the channel.

Figure 6A:
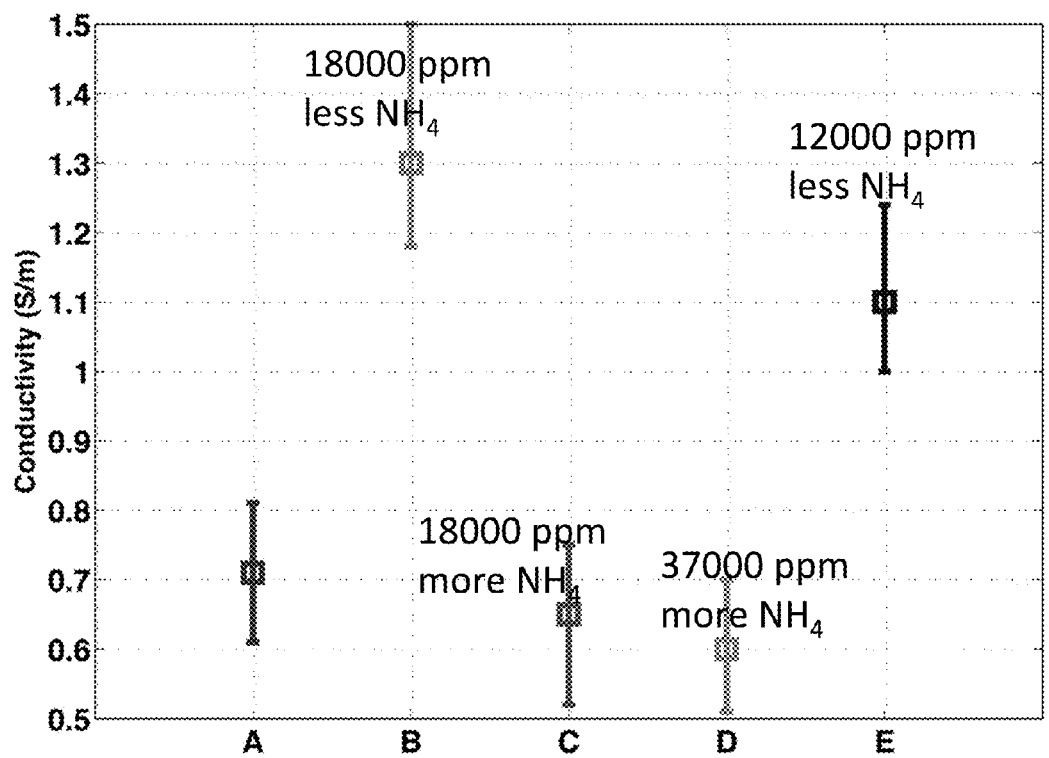
FIGS. 6A and 6B are graphs illustrating exemplary conductivity values measured in a channel at different concentrations of an exemplary analyte.
Figure 6B:
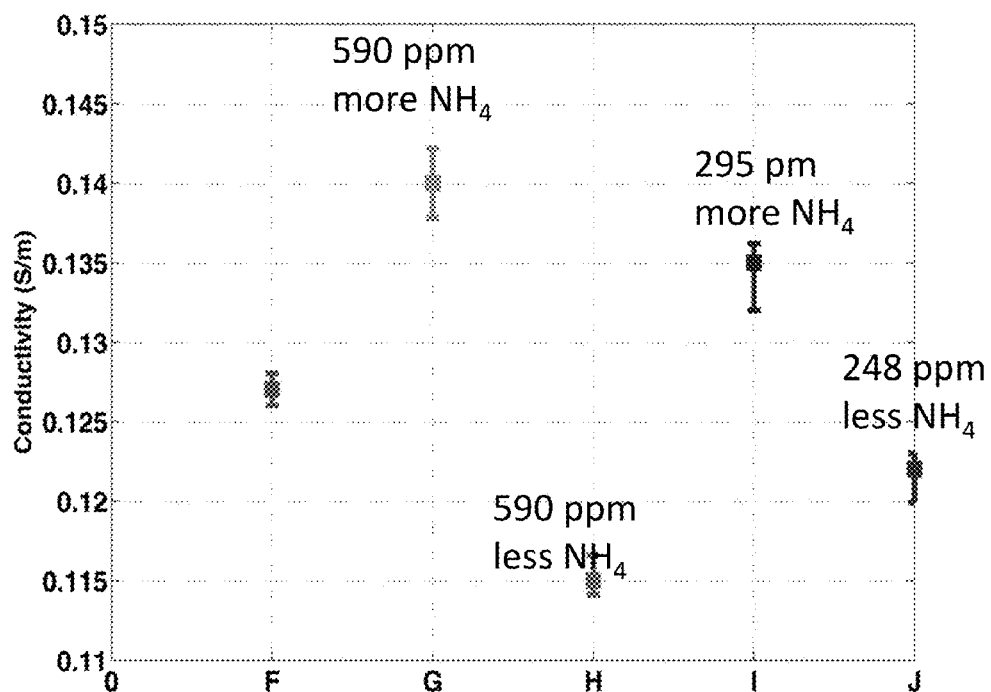

FIGS. 6A and 6B are graphs showing conductivity values measured in a channel for different test cases. In each test case, a different relative concentration of an analyte relative to concentrations of two additional substances (in this case, ammonium and hydrogen peroxide) is used, and the corresponding conductivity value is determined in the channel. In one embodiment, Standard Clean 1 or SC1 is used a solution in the test cases. Details of SC1 can be found at http://en.wikipedia.org/wiki/RCA_clean, the entire contents of which are expressly incorporated herein by reference. The ratios of concentrations among the three substances in the test cases represented in FIGS. 6A and 6B are presented in Table 1 below.

TABLE 1

Test case ratios for the concentration of SC1 to the concentration of hydrogen peroxide to the concentration of ammonium

| Test Case | Concentration Ratio of Water:Hydrogen Peroxide:Ammonium Hydroxide |
|---|---|
| A | 5:1:1 |
| B | 4.8:1.3:0.75 |
| C | 5.1:0.62:1.3 |
| D | 5.26:0.24:1.5 |
| E | 4.92:1.3:0.83 |

TABLE 1-continued

Test case ratios for the concentration of SC1 to the concentration of hydrogen peroxide to the concentration of ammonium

| Test Case | Concentration Ratio of Water:Hydrogen Peroxide:Ammonium Hydroxide |
|---|---|
| F | 3500:10:10 |
| G | 3501:3.95:14 |
| H | 3497:16:06 |
| I | 3501:6.97:12 |
| J | 3499:12.5:8.3 |

The lower the concentration of an analyte, the easier it is to measure differences in relative concentrations between the analyte and other substances. For example, at concentration ratios of about 1000:1:1, detection sensitivity on the order of 1-10 ppm may be achieved in the exemplary detection system. At concentration ratios of about 350:1:1, detection sensitivity on the order of 100 ppm may be achieved. At concentration ratios of about 5:1:1, detection sensitivity on the order of 10,000 ppm may be achieved.

The substrate 102, the channel 104 and the cover slip 114 may be formed of glass in certain embodiments. Biological conditions represent a barrier to the use of glass-derived implantations due to the slow dissolution of glass into biological fluids and adhesion of proteins and small molecules to the glass surface. In exemplary embodiments, surface modification using a self-assembled monolayer offers an approach for modifying glass surfaces for silver detection and analysis. In certain embodiments, at least a portion of the inner surface 106 of the channel 104 and/or the inner surface of the cover slip 114 may be pre-treated or covalently modified to include or be coated with a material that enables specific covalent binding of a sensor compound (e.g., TPEA2) to the inner surface.

Exemplary materials that may be used to modify the inner surface of the channel and/or the cover slip include, but are not limited to, a silane compound (e.g., tricholorsilane, alkylsilane, triethoxysilane, perfluoro silane), zwitterionic sultone, poly(6-9)ethylene glycol (Peg), perfluorooctyl, fluorescein, an aldehyde, a graphene compound, and the like. The covalent modification of the inner surface of the channel may prevent non-specific absorption of certain molecules. In one example, covalent modification of the inner surface may enable covalent bonding of sensor compound molecules to the inner surface while prevent non-specific absorption of other molecules to the inner surface.

As one example of a modification material, alkysilanes are a group of molecules that form covalent monolayers on the surfaces of silicon and glass. Alkylsilanes have three distinct regions: a head group surrounded by good leaving groups, a long alkyl chai, and a terminal end group. The head group, usually containing a halogen, alkoxy or other leaving group, allows the molecule to covalently anchor to the solid glass surface under appropriate reaction conditions. The alkyl chain contributes to the stability and ordering of the monolayer through Vander-Waals interactions, which allows for the assembly of a well ordered monolayer. The terminal end group allows for the functionalization and tunability of chemical surface properties by using techniques including, but not limited to, nucleophilic substitution reactions, click chemistry or polymerization reactions.

In one exemplary technique of treating the inner surface with a silane compound, a solution is produced. The solution may be between 0.1% and 4% v/v (if silane is liquid) or w/v (if silane is a solid) of appropriate chloro-, trichloro-, trimethoxy- or triethoxysilane in the appropriate solvent (e.g. toluene for trimethoxy- or triethoxysilanes, ethanol for chloro- or trichlorosilanes or water with a pH between 3.5 to 5.5 for trimethoxysilanes). The solution may be filtered through a 0.2 micron surfactant free cellulose acetate (SFCA) filter. About 10 SEL of the filtered silane solution may be added to a port of the channel and allowed to capillary fill the channel. This may or may not be observed by light microscopy and may take between five and forty minutes depending upon the solvent composition. After capillary filling is complete, about 10 μL of the filtered silane solution may be added to the remaining ports of the channel. The entire channel may then be immersed in the filtered silane solution and allowed to react for a desired amount of time (for example, about 1 to 24 hours) at a desired temperature (for example, about 20° C. to 80° C. depending upon the specific silane and solvent composition used for the modification). After the desired reaction time is over, the silanization process may be quenched using one of the following techniques, and catalytic amount of acetic acid may be added to toluene or ethanol-based surface modifications in some cases.

In one exemplary technique of quenching, the entire channel may be transferred to a container filled with 0.2 micron SFCA filtered ethanol, and stored until the desired time for use or further modification. In another exemplary technique of quenching, the channel may be electrokinetically washed with an appropriate solvent composition. In one electrokinetic washing technique for toluene modification of a channel, toluene is electrokinetically driven through the channel at a 10V to 1000V differential between electrodes for about 5 to 15 minutes, followed by electrokinetically driving ethanol through the channel at a 10V to 1000V differential between electrodes for about 5 to 15 minutes, followed by electrokinetically driving a 1:1 mixture of ethanol:water through the channel at 10V to 1000V differential between electrodes for about 5 to 15 minutes, followed by a final electrokinetic driving of water through the channel at 10V to 1000V for about 5 to 15 minutes. Proper operation of the channel may be confirmed by measuring the current at 1000V applied field to an added 50 mM sodium borate buffer in the channel (giving a current reading of approximately 330 nA based on channel dimensions) and re-addition of ultrapure (e.g., MILLIQ ultrapure) water at the same applied field affording a current of less than about 20 nA.

Table 2 summarizes certain exemplary materials that may be used to modify an inner surface of a channel and/or an inner surface of a cover slip covering the channel.

TABLE 2

Exemplary materials for modification of channel

| Modification | Structure |
|---|---|
| Poly(6-9)ethylene glycol (Peg) | (structure shown) |
| Octyldimethyl (ODM) | (structure shown) |
| Octyldimethyl + Peg 100,000 | ODM + Poly(ethylene oxide) (average MW 100,000) grafted under radical conditions |
| Octyldimethyl + Peg 400,000 | ODM + Poly(ethylene oxide) (average MW 400,000) grafted under radical conditions |
| Octyldimethyl + Peg 600,000 | ODM + Poly(ethylene oxide) (average MW 600,000) grafted under radical conditions |
| Octyldimethyl + Peg 1,000,000 | ODM + Poly(ethylene oxide) (average MW 1,000,000) grafted under radical conditions |
| Octyldimethyl + PVP 1,300,000 | ODM + Polyvinylpyrrolidone (average MW 1,300,000) grafted under radical conditions |
| 3-(dimethylaminopropyl) | (structure shown) |
| 3-(aminopropyl) | (structure shown) |

TABLE 2-continued
Exemplary materials for modification of channel
| Modification | Structure |
|---|---|
| Perfluorooctyl | 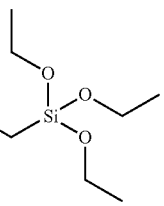 |
| Perfluorodecyl | 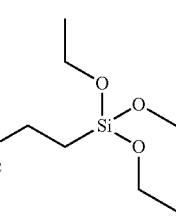 |
| 3-(trifluoromethyl)propyl | 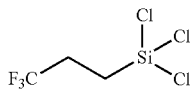 |
| 3-cyanopropyl | 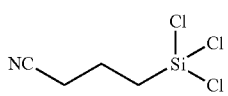 |
| Propylmethacrylate | 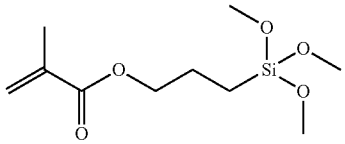 [SMILES: C=C(C)C(=O)OCCC[Si](OC)(OC)OC] |
| 3-mercaptopropyl | 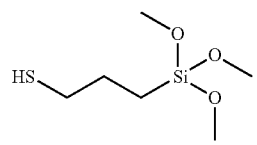 |
| 3-mercaptopropyl + Peg 5000 Maleimide | 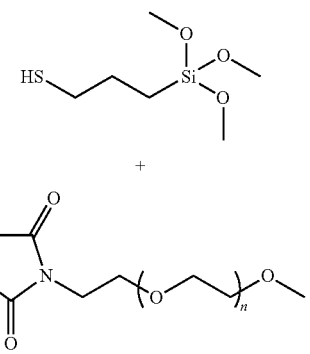 |
| 3-mercaptopropyl + acrylamide | 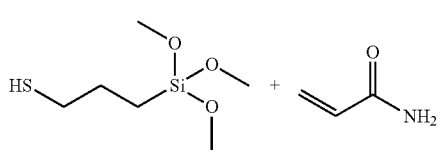 |

TABLE 2-continued

Exemplary materials for modification of channel

| Modification | Structure |
|---|---|
| 3-mercaptopropyl + trimethylammonium | |
| Zwitterionic sultone | 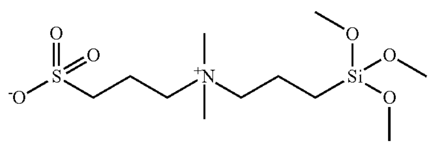 |
| Zwitterionic phosphate | 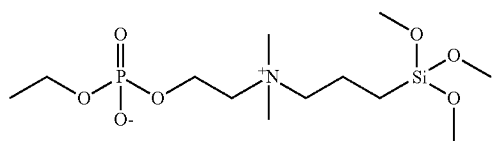 [SMILES: CCOP(=O)([O-])OCC[N+](C)(C)CCC[Si](OC)(OC)OC] |

III. Exemplary Silver Detection Techniques

Exemplary techniques enable detection of silver (I) ions in a sample using one or more sensor compounds (e.g., TPEA2). In certain cases, TPEA2 molecules and silver (I) ions interact to form an aggregate that substantially blocks fluid flow in the channel and consequently causes an electrical current and conductivity to decrease. A schematic structure of a TPEA2 molecule is reproduced below.

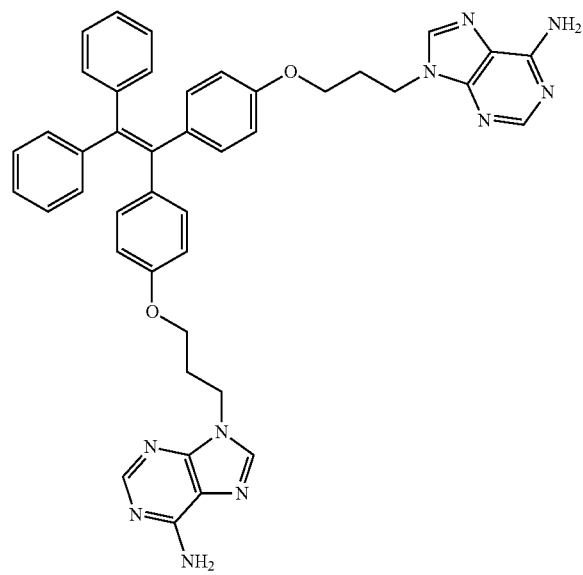 [SMILES: Nc1ncnc2c1ncn2CCCOc1ccc(C(=C(c2ccccc2)c2ccccc2)c2ccc(OCCCn3cnc4c(N)ncnc43)cc2)cc1]

In certain embodiments, the electrodes used in the detection system may be metallic, for example, aluminum, manganese and platinum.

Exemplary techniques may introduce both the sample and the sensor compound (e.g., TPEA2) into a channel in the detection system that is especially configured and dimensioned to allow silver detection. In certain embodiments, the channel may be configured so that its depth and/or its width are substantially equal to or lower than a diameter of the aggregate particle. Upon introduction of both the sample and the sensor compound into the channel, formation of the aggregate may indicate presence of silver ions in the sample, while absence of the aggregate may indicate absence of silver ions in the sample.

When flow of the fluid and/or flow of the charged particles in the fluid is uninhibited (for example, due to absence of an aggregate), the conductive particles or ions in the fluid may travel along at least a portion of the length of a channel in a detection system along the y-axis from an input port toward an output port. The movement of the conductive particles or ions may result in a first or "reference" electrical property value or range of values (e.g., of an electrical current, conductivity, resistivity) being detected (for example, by a silver detection circuit) along at least a portion of the length of the channel. In some embodiments, electrical property values may be continually or periodically monitored during a time period until the values reach equilibrium (for example, by an equilibration circuit). One of the detected values may be selected as the reference electrical property value to avoid the influence of transient changes in the electrical property.

The term "reference" electrical property value may refer to a value or range of values of an electrical property of a channel prior to introduction of both a sample and a sensor compound in the channel. That is, the reference value is a value characterizing the channel prior to any interaction between silver in the sample and the sensor compound. In some cases, the reference value may be detected at a time period after introduction of the sensor compound into the channel but before introduction of the sample into the channel. In some cases, the reference value may be detected at a time period after introduction of the sample into the channel but before introduction of the sensor compound into the channel. In some cases, the reference value may be detected at a time period before introduction of either the sample or the sensor compound into the channel. In some cases, the reference value may be predetermined and stored on a non-transitory storage medium from which it may be accessed.

However, when flow of the fluid and/or flow of the charged particles in the fluid is partially or completely blocked (for example, by formation of an aggregate), the conductive particles or ions in the fluid may be unable to freely travel along at least a portion of the length of the channel along the y-axis from the input port toward the output port. The hindered or stopped movement of the conductive particles or ions may result in a second electrical property value or range of values (e.g., of an electrical current, conductivity, resistivity) being detected along at least a portion of the length of the channel. In some embodiments, a waiting or adjustment time period may be allowed to pass after introduction of both the sample and the sensor compound into the channel prior to detecting the second electrical property value. The waiting or adjustment time period allows an aggregate to form in the channel and for the aggregate formation to alter the electrical properties of the channel.

In some embodiments, one or more electrical property values may be continually or periodically monitored during a time period after the introduction of both the sample and the sensor compound until the values reach equilibrium. One of the detected values may be selected as the second electrical property value to avoid the influence of transient changes in the electrical property.

The second electrical property value may be compared to the reference electrical property value. If it is determined that the difference between the second value and the reference value corresponds to a predetermined range of decrease in current or conductivity (or increase in resistivity), it may be determined that a silver aggregate is present in the channel and that, therefore, silver ions are present in the sample.

In certain embodiments, prior to use of a detection system, the channel may be free of the sensor compound (e.g., TPEA2). That is, a manufacturer of the detection system may not pre-treat or modify the channel to include the sensor compound. In this case, during use, a user may need to introduce both the sensor compound and the sample into the channel.

In one example, the user may introduce the sensor compound (e.g., TPEA2) and the sample into the channel concurrently, for example, in a mixture of the sensor compound and the sample. In this case, a reference electrical property value may be detected in the channel prior to introduction of the mixture, and an electrical property value may be detected after introduction of the mixture. Comparison of the electrical property value to the reference electrical property value may be used to determine if silver is present in the sample.

In another example, the user may introduce the sensor compound (e.g., TPEA2) and the sample into the channel concurrently, for example, in a mixture of the sensor compound and the sample. A stored reference electrical property value characterizing the channel prior to introduction of both the sample and the sensor compound may be retrieved or accessed from a non-transitory storage medium. An electrical property value may be detected after introduction of the mixture of the sample and the sensor compound into the channel. Comparison of the electrical property value to the stored reference electrical property value may be used to determine if silver is present in the sample.

In another example, the user may first introduce the sensor compound (e.g., TPEA2) into the channel, and detect a reference electrical property value with only the sensor compound in the channel. The user may subsequently introduce the sample into the channel, and detect an electrical property value after waiting for a time period after introduction of the sample into the channel. Comparison of the electrical property value to the reference electrical property value may be used to determine if silver is present in the sample.

In another example, the user may first introduce the sensor compound (e.g., TPEA2) into the channel, and may subsequently introduce the sample into the channel. The user may then detect an electrical property value after waiting for a time period after introduction of the sample into the channel. A stored reference electrical property value characterizing the channel prior to introduction of both the sample and the sensor compound may be retrieved or accessed from a non-transitory storage medium. Comparison of the stored electrical property value to the reference electrical property value may be used to determine if silver is present in the sample.

In another example, the user may first introduce the sample into the channel, and detect a reference electrical property value with only the sample in the channel. The user may subsequently introduce the sensor compound (e.g., TPEA2) into the channel, and detect an electrical property value after waiting for a time period after introduction of the sensor compound into the channel. Comparison of the electrical property value to the reference electrical property value may be used to determine if silver is present in the sample.

In another example, the user may first introduce the sample into the channel, and may subsequently introduce the sensor compound (e.g., TPEA2) into the channel. The user may then detect an electrical property value after waiting for a time period after introduction of the sensor compound into the channel. A stored reference electrical property value characterizing the channel prior to introduction of both the sample and the sensor compound may be retrieved or accessed from a non-transitory storage medium. Comparison of the stored electrical property value to the reference electrical property value may be used to determine if silver is present in the sample.

In certain other embodiments, prior to use of the detection system, the channel may be pre-treated or modified so that at least a portion of an inner surface of the channel includes or is coated with the sensor compound (e.g., TPEA2). That is, a manufacturer of the detection system may pre-treat or modify the channel to include the sensor compound. In this case, a user may only need to introduce the sample into the channel.

In one example, the manufacturer may detect a reference electrical property value of the channel with the sensor compound (e.g., TPEA2) and may store the reference electrical property value on a non-transitory storage medium. During use, the user may introduce the sample into the channel and detect an electrical property value after waiting for a time period after introduction of the sample into the channel. The stored reference electrical property value may be accessed or retrieved from the storage medium. Comparison of the electrical property value to the reference electrical property value may be used to determine if silver is present in the sample.

In another example, the user may detect a reference electrical property value of the channel with the sensor compound (e.g., TPEA2) prior to introducing the sample into the channel. The user may subsequently introduce the sample into the channel and detect an electrical property value after waiting for a time period after introduction of the sample into the channel. Comparison of the electrical property value to the reference electrical property value may be used to determine if silver is present in the sample.

Figure 7A:
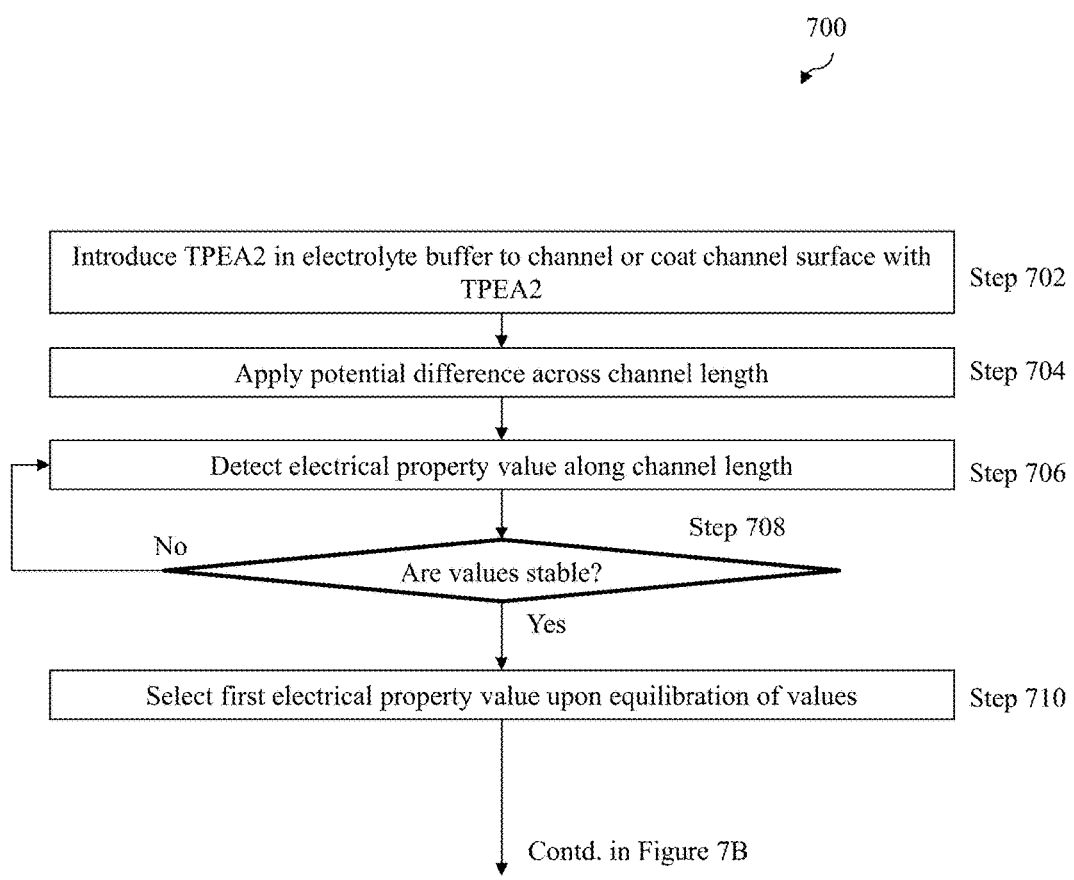
FIGS. 7A, 7B, 8A, 8B, and 9-16 are flowcharts illustrating exemplary methods for detecting silver in a sample.
Figure 7B:
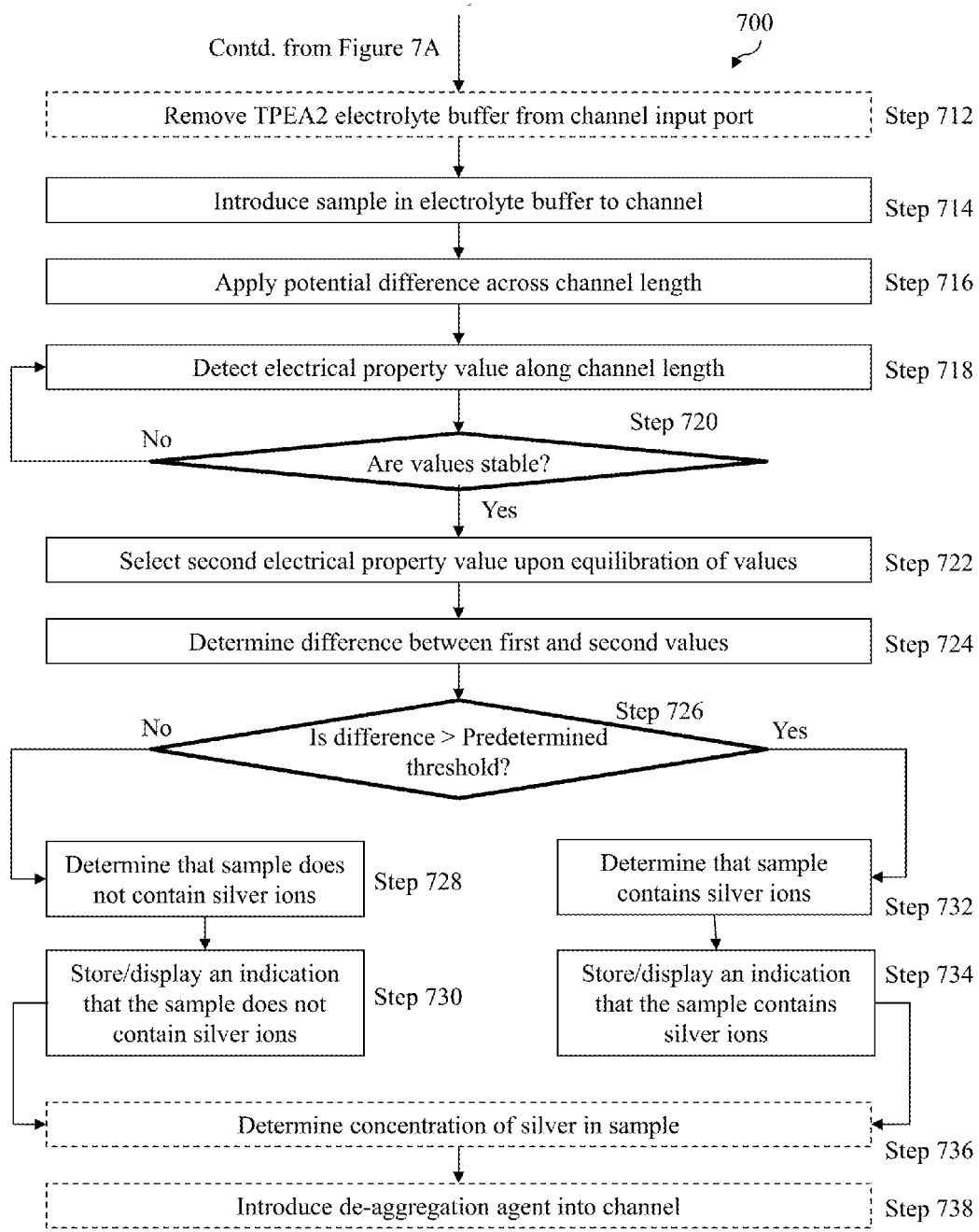

FIGS. 7A and 7B are flowcharts illustrating an exemplary method 700 for detecting the presence or absence of silver in a sample. In step 702, a sensor compound (e.g., TPEA2) in an electrolyte buffer may be introduced into the channel using any suitable technique, for example, capillary filing or electro-kinetic filling. Alternatively, in step 702, at least a portion of an inner surface of the channel may be treated to include or be coated with the sensor compound (e.g., TPEA2). In step 704, a potential difference may be applied across at least a portion of the length of the channel using a voltage source. In step 706, while the potential difference is being applied, one or more electrical properties values (e.g., the electrical current and/or conductivity) along at least a portion of the length of the channel may be detected. In some cases, the electrical current and/or conductivity may be directly measured. In other cases, a measure indicating the electrical current and/or a measure indicating the electrical conductivity may be detected.

Introduction of the sensor compound into the channel may cause transient changes in the electrical properties of the channel. In order to obtain an accurate and reliable measure of the electrical properties, in step 708, a first set of two or more values that were detected in step 706 may be continually or periodically monitored. It may be determined if the electrical property values have reached equilibrium, i.e., has stopped varying outside of a predetermined variance or tolerance range. If it is determined that the electrical property values have not reached equilibrium, then the method may return to step 706 to detect additional electrical property values. On the other hand, if it is determined that the electrical property values have reached equilibrium, then the method may proceed to step 710.

In step 710, a first or reference value may be selected from the first set of electrical property. The first electrical property value may be used to represent the one or more electrical properties (e.g., electrical current or conductivity) of the channel prior to any introduction of both of the sample and the sensor compound into the channel.

In an alternative embodiment, the first value or reference value may be accessed from a non-transitory storage or memory, and may not need to be detected in steps 704-710, thereby making steps 704-710 unnecessary in this embodiment.

In step 712, in some embodiments, the electrolyte buffer including the TPEA2 molecules may be removed from the input port of the channel at which it was introduced so that subsequent introduction of the sample at the input port does not cause interaction between the TPEA2 molecules and the sample at the input port. That is, any such interaction will take place within the length of the channel and not at the input port.

In step 714, a sample in an electrolyte buffer may be introduced into the channel using any suitable technique, for example, capillary filing or electro-kinetic filling.

Although the method illustrated in FIGS. 7A and 7B indicates that the sensor compound is introduced into the channel prior to introduction of the sample, another embodiment of the method may involve introducing the sample into the channel prior to introduction of the sensor compound. That is, the sample may be introduced into the channel in step 702 and the sensor compound may be introduced into the channel in step 714. Yet another embodiment may involve pre-mixing the sample and the sensor compound, and introducing the pre-mixture at one time into the channel. In the pre-mixing case, a reference electrical property value may be detected prior to introduction of the pre-mixture into the channel, and a second electrical property value may be detected after introduction of the pre-mixture into the channel. The second value may be compared to the reference value to determine if silver is present in the sample.

In step 716, a potential difference may be applied across at least a portion of the length of the channel using a voltage source. In step 718, while the potential difference is being applied, one or more electrical properties (e.g., electrical current and/or conductivity) along at least a portion of the length of the channel may be detected. In some cases, the electrical current and/or conductivity may be directly measured. In other cases, a measure indicating the electrical current and/or a measure indicating the electrical conductivity may be detected.

Introduction of the sample into the channel may cause transient changes in the electrical current conducted along the channel. In order to obtain an accurate and reliable measure of the electrical properties, in step 720, a second set of two or more values that were detected in step 718 may be continually or periodically monitored. It may be determined if the electrical property values have reached equilibrium, i.e., has stopped temporally varying outside of a predetermined variance or tolerance range. If it is determined that the electrical property values have not reached equilibrium, then the method may return to step 718 to detect additional values. On the other hand, if it is determined that the electrical property values have reached equilibrium, then the method may proceed to step 722. In step 722, a second value may be selected from the second set of values of the electrical property. The second value may be used to represent the one or more electrical properties (e.g., electrical current or conductivity) along at least a portion of the length of the channel after both the sample and the sensor compound have been introduced into the channel.

In step 724, a difference between the magnitude of the first or reference value (determined in step 710) and the magnitude of the second value (determined in step 722) may be determined. In step 726, it may be determined if the difference determined in step 724 satisfies a predetermined threshold, for example, if the difference is above a predetermined value or if the difference is within a predetermined range.

If the sample includes silver ions that undergo a particular type of interaction with the sensor compound, introduction of both the sample and the sensor compound into the channel may cause the particular type of interaction. Conversely, if the sample does not include silver ions, introduction of both the sample and the sensor compound into the channel may not cause the particular type of interaction. Thus, if the particular interaction causes a change in an electrical current or conductivity in the channel, then detection of the expected change in step 726 may indicate presence of silver ions in the sample.

As such, if it is determined in step 726 that the difference between the first and second values is greater than the predetermined threshold, then it may be determined in step 732 that the sample contains silver ions. Subsequently, in step 734, an indication that the sample contains silver may be stored on a non-transitory storage medium. Alternatively or additionally, in step 734, an indication that the sample contains silver ions may be displayed on a display device.

On the other hand, if it is determined in step 726 that the difference between the first and second values is lower than the predetermined threshold, then it may be determined in step 728 that the sample does not contain silver ions. Subsequently, in step 730, an indication that the sample does not contain silver ions may be stored on a non-transitory storage medium. Alternatively or additionally, in step 730, an indication that the sample does not contain silver ions may be displayed on a display device.

Exemplary thresholds may include, but are not limited to, 5-100 nA in certain non-limiting cases. In one example, a 100-nm channel may be capillary filled with an electrolyte buffer (e.g., sodium tetraborate dissolved in water and tetrahydrofuran with a ratio of 5:1 45 mM sodium tetraborate:tetrahydrofuran) for approximately five or ten minutes by addition of approximately 10 µL of electrolyte buffer to one of the channel ports. Upon complete channel filling, approximately 10 µL of electrolyte buffer is added to the other channel port and electrodes connected to a Kiethley 2410 ammeter are then inserted into the ports of the channel and a differential of about +1000 V or −1000 V is applied until a stable current is obtained (approximately 45 nA for +1000 V and approximately −45 nA for −1000 V). Approximately 40 µM TPEA2 in 5:1 50 mM borate:tetrahydrofuran is introduced into the channel and a potential differential of about +1000 V or −1000 V volts is applied until a stable current is obtained (approximately 40 to 43 nA for +1000 V and approximately −40 to −43 nA for −1000 V).

The TPEA2 buffer may be removed from just one or both channel ports and replaced with approximately 5 µL of a sample solution. The sample solution may or may not contain silver ions. In one example, if the sample solution is one that contains silver ions, the sample solution may contain approximately 200 µM silver (I) nitrate in electrolyte buffer (approximately 5:1 ratio of about 50 mM sodium borate:tetrahydrofuran). After the sample solution is introduced into the channel, a potential difference of about +1000V may be applied across the electrodes and the field is intermittently switched to −1000V to induce mixing. Approximately 30 second cycles may be used at +1000V and −1000V to induce sample mixing, and the electrical current along at least a portion of the length of the channels may be detected at both applied fields. With an applied field of approximately +1000V, electrical current of approximately 43 to 46 nA is detected in certain cases, and with an applied field of −1000V, electrical current of approximately −60 to −63 nA is detected in certain cases.

In certain embodiments, the channel may be prepared for reuse for subsequent testing of samples. In step 738, one or more de-aggregation agents may be introduced into the channel using any suitable technique, for example, capillary filing or electro-kinetic filling. The de-aggregation agents may be selected so that interaction between the de-aggregation agents and the aggregate formed in the channel causes the aggregate to dissolve or disintegrate. Subsequently, the channel may be filled with an electrolyte buffer to flush out the channel and allow a sample and a sensor compound to be introduced into the channel. In one example, a channel including an aggregate may be prepared for reuse by washing the channel with dimethylsulfoxide introduced into the channel with a potential difference of about 500 V applied between the input and output nodes, followed by washing with about 10 mM sodium hydroxide introduced into the channel with a potential difference of about 500 V applied between the input and output nodes, followed by washing with about 1 M hydrogen chloride introduced into the channel with a potential difference of about 100 V applied between the input and output nodes.

In another example, a channel including an aggregate may be prepared for reuse by washing the channel with dimethylsulfoxide introduced into the channel for about ten minutes with a potential difference of about 500 V applied between the input and output nodes, followed by washing with about 1 M hydrogen chloride introduced into the channel for about 10 minutes with a potential difference of about 100 V applied between the input and output nodes, followed by washing with about 100 mM sodium tetraborate introduced into the channel for about 10 minutes with a potential difference of about 500 V applied between the input and output nodes, followed by about 18 MILLIQ MEGAOHM water introduced into the channel for about 10 minutes with a potential difference of about 500 V applied between the input and output nodes.

In certain embodiments, in step 736, prior to disintegration of the aggregate, an absolute or relative concentration of silver ions may be determined based on an electrical property value of the channel. The concentration of silver ions may be determined in such a manner because the channels of exemplary detection systems have a high inner surface area to volume ratio. At low concentrations of silver, electrical conductivity in the channel is dominated by surface charges. As such, measurements of electrical properties of the channel can enable distinction between different ions. As a result, unique and sensitive measurements of the bulk flow in the channel can be used to determine information on the surface charges at the inner surface of the channel. Exemplary embodiments may thus compute predetermined ranges of electrical property values of the channel that are characteristic of silver ions given the dimensions of the channel and at different concentrations of silver ions. These predetermined values may then be used to determine an unknown concentration of silver ions in a sample.

Detailed information on surface charges in the channel for different ions is presented in the following papers, the entire contents of which are expressly incorporated herein by reference: "Surface-dependent chemical equilibrium constants and capacitances for bare and 3-cyanopropyldimethylchlorosilane coated silica nanochannels," M. B. Andersen, J. Frey, S. Pennathur and H. Bruus, J., Colloid Interface Sci. 353, 301-310 (2011), and "Hydronium-domination ion transport in carbon-dioxide-saturated electrolytes at low salt concentrations in nanochannels," K. L. Jensen, J. T. Kristensen, A. M. Crumrine, M. B. Andersen, H. Bruus and S. Pennathur, Phys. Review E. 83, 5, 056307.

FIG. 5 is a schematic drawing of the inside of a channel including an inner surface of the channel 502, an immobile layer of fluid 504 lying immediately adjacent to the inner surface of the channel, a diffusive layer of fluid 506 lying immediately adjacent to the immobile layer, and a bulk fluid flow layer 508 lying immediately adjacent to the diffusive layer. Exemplary ions are represented in each of the fluid layers. Upon application of a potential difference across the length of the channel, an electrical property value may be detected along at least a portion of the channel (for example, by the silver detection circuit 122). The comparison circuit 124 may be used to compare the measured electrical property value to a predetermined range of electrical property values that correspond to a particular concentration or range of concentration values of silver ions. The concentration determined may be an absolute concentration of silver ions or a relative concentration of silver ions with respect to the concentrations of one or more other substances in the channel.

FIGS. 6A and 6B are graphs showing conductivity values measured in a channel for different test cases. In each test case, a different relative concentration of an analyte relative to concentrations of two additional substances (in this case, ammonium and hydrogen peroxide) is used, and the corresponding conductivity value is determined in the channel. In one embodiment, Standard Clean 1 or SC1 is used a solution in the test cases. Details of SC1 can be found at http://en.wikipedia.org/wiki/RCA_clean, the entire contents of which are expressly incorporated herein by reference. The ratios of concentrations among the three substances in the test cases represented in FIGS. 6A and 6B are presented in Table 1 above.

The lower the concentration of an analyte, the easier it is to measure differences in relative concentrations between the analyte and other substances. For example, at concentration ratios of about 1000:1:1, detection sensitivity on the order of 1-10 ppm may be achieved in the exemplary detection system. At concentration ratios of about 350:1:1, detection sensitivity on the order of 100 ppm may be achieved. At concentration ratios of about 5:1:1, detection sensitivity on the order of 10,000 ppm may be achieved.

Another exemplary technique for detecting silver ions may involve detection of the presence of a diode-like behavior in the channel that is caused by the formation of a silver aggregate in the channel. In the absence of an aggregate, application of a potential difference having a substantially similar magnitude (e.g., +500 V) may result in a substantially same magnitude of an electrical property (e.g., current) detected along the length of the channel regardless of the direction of application of the potential difference or electric field. If the potential difference is applied across the length of the channel in a first direction along the length of the channel (e.g., such that the positive electrode is at an input port 110 at or near a first end of the channel and such that the negative electrode is at an output port 112 at or near a second end of the channel), the resulting current may be substantially equal in magnitude to the resultant current if the potential difference is applied in the opposite direction (e.g., such that the positive electrode is at the output port 112 and such that the negative electrode is at the input port 110).

Formation of an aggregate in the channel may cause a diode-like behavior in which reversal of the direction of the applied potential difference or electric field causes a change in the electrical property detected in the channel. The diode-like behavior causes the detected electrical current to vary in magnitude with the direction of the electric field. When the electric field or potential difference is applied in the first direction, the magnitude of the electrical current may be different in magnitude than when the potential different or electric field is applied in the opposite direction. Thus, comparison between a first electrical property value (detected when a potential difference is applied in a first direction along the channel length) and a second electrical property value (detected when a potential difference is applied in a second opposite direction along the channel length) may enable detection of an aggregate, and thereby detection of silver ions in the sample. If the first and second electrical property values are substantially equal in magnitude, then it may be determined that the sample does not contain silvers ions. On the other hand, if the first and second electrical property values are substantially unequal in magnitude, then it may be determined that the sample contains silver ions. In other words, the sum of the values of the electrical property (positive in one direction, negative in the other direction) is substantially zero in the absence of an aggregate and substantially non-zero in the presence of an aggregate.

Figure 8A:
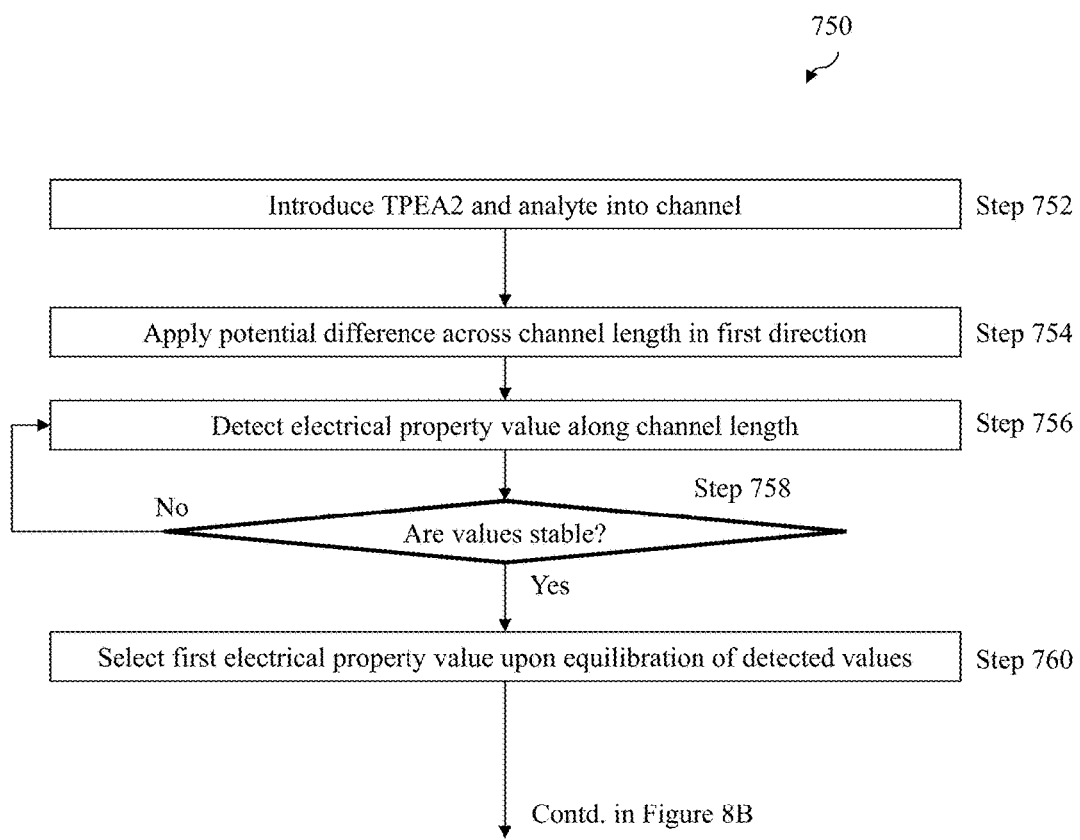
Figure 8B:
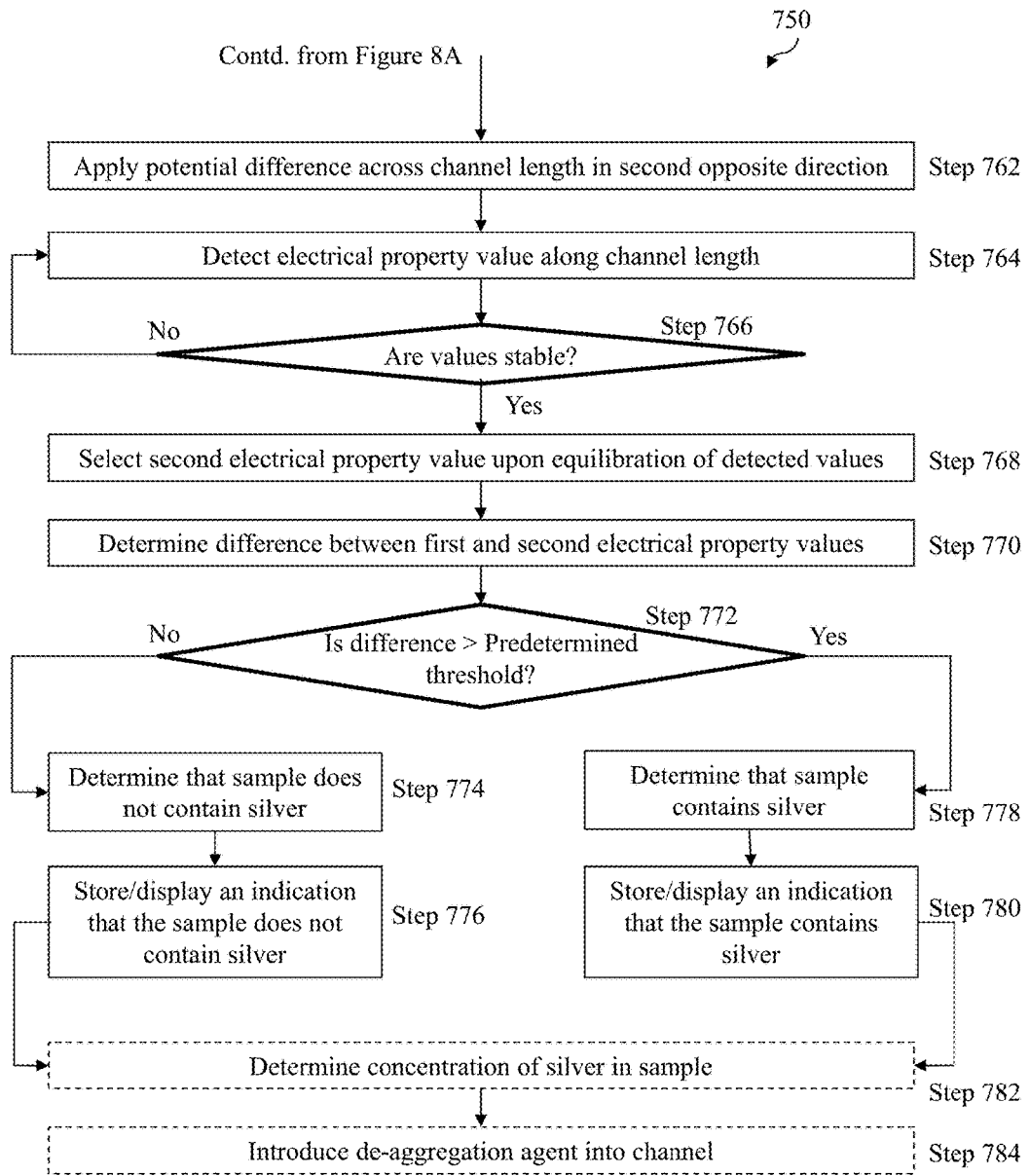

FIGS. 8A and 8B are flowcharts illustrating a general exemplary method 750 for detecting the presence or absence of silver ions in a sample. In step 752, a sensor compound in an electrolyte buffer and a sample may be introduced into the channel using any suitable technique, for example, capillary filing or electro-kinetic filling. The sensor compound and the sample may be introduced concurrently or separately. In one embodiment, at least a portion of an inner surface of the channel may be treated to include or be coated with the sensor compound. In step 754, a potential difference may be applied across at least a portion of the length of the channel using a voltage source in a first direction along the channel length (y-axis). In step 756, while the potential difference is being applied, one or more electrical properties values (e.g., the electrical current and/or conductivity) along at least a portion of the length of the channel may be detected. In some cases, the electrical current and/or conductivity may be directly measured. In other cases, a measure indicating the electrical current and/or a measure indicating the electrical conductivity may be detected.

In order to obtain an accurate and reliable measure of the electrical properties, in step 758, a first set of two or more values that were detected in step 756 may be continually or periodically monitored. It may be determined if the electrical property values have reached equilibrium, i.e., has stopped varying outside of a predetermined variance or tolerance range. If it is determined that the electrical property values have not reached equilibrium, then the method may return to step 756 to detect additional electrical property values. On the other hand, if it is determined that the electrical property values have reached equilibrium, then the method may proceed to step 760.

In step 760, a first value may be selected from the first set of electrical property. The first electrical property value may be used to represent the one or more electrical properties (e.g., electrical current or conductivity) of the channel when an electric field is applied in a first direction along the channel length (y-axis).

In step 762, a potential difference may be applied across at least a portion of the length of the channel using a voltage source in a second opposite direction along the channel length (y-axis). The second direction may be substantially opposite to the first direction. In step 764, while the potential difference is being applied, one or more electrical properties (e.g., electrical current and/or conductivity) along at least a portion of the length of the channel may be detected. In some cases, the electrical current and/or conductivity may be directly measured. In other cases, a measure indicating the electrical current and/or a measure indicating the electrical conductivity may be detected.

In order to obtain an accurate and reliable measure of the electrical properties, in step 766, a second set of two or more values that were detected in step 764 may be continually or periodically monitored. It may be determined if the electrical property values have reached equilibrium, i.e., has stopped temporally varying outside of a predetermined variance or tolerance range. If it is determined that the electrical property values have not reached equilibrium, then the method may return to step 764 to detect additional values. On the other hand, if it is determined that the electrical property values have reached equilibrium, then the method may proceed to step 768. In step 768, a second value may be selected from the second set of values of the electrical property. The second value may be used to represent the one or more electrical properties (e.g., electrical current or conductivity) along at least a portion of the length of the channel after both the sample and the sensor compound have been introduced into the channel.

In step 770, a difference between the magnitude of the first value (determined in step 760) and the magnitude of the second value (determined in step 768) may be determined. In step 772, it may be determined if the difference determined in step 770 satisfies a predetermined threshold, for example, if the difference is above a predetermined value or if the difference is within a predetermined range.

If it is determined in step 772 that the difference between the first and second values satisfies the predetermined threshold (e.g., that the difference in magnitudes is substantially non-zero), then it may be determined in step 778 that the sample contains silver ions. Subsequently, in step 780, an indication that the sample contains silver ions may be stored on a non-transitory storage medium. Alternatively or additionally, in step 780, an indication that the sample contains silver ions may be displayed on a display device.

On the other hand, if it is determined in step 772 that the difference between the first and second values does not satisfy the predetermined threshold (e.g., that the difference in magnitudes is substantially zero), then it may be determined in step 774 that the sample does not contain silver ions. Subsequently, in step 776, an indication that the sample does not contain silver ions may be stored on a non-transitory storage medium. Alternatively or additionally, in step 776, an indication that the sample does not contain silver ions may be displayed on a display device.

In certain cases, if the difference in magnitude between the first and second values is greater than the threshold, then it may be determined that the sample contains silver ions. Otherwise, it may be determined that the sample does not contain silver ions. In certain non-limiting examples, the threshold may be approximately 1 nA to approximately 3 nA.

In one example in which the presence of silver (I) ions is detected by TPEA2, interaction between the silver ions and TPEA2 result in the formation of an aggregate in the channel. In the absence of the silver aggregate, the first and second electrical property values may be substantially equal. For example, when the channel is filled with a 5:1 45 mM sodium tetraborate:tetrahydrofuran (lacking an aggregate), a first current value of about 45 nA may be detected when a potential difference of about +1000 V is applied in a first direction, and a second current value of about −45 nA may be detected when a potential difference of about −1000V is applied in a second opposite direction. Similarly, when the channel is filled with a 40 µM TPEA2 in 5:1 50 mM borate:tetrahydrofuran (lacking a sensor compound and lacking an aggregate), a first current value of about 40 nA to about 43 nA may be detected when a potential difference of about +1000 V is applied in a first direction, and a second current of about −40 nA to about −43 nA may be detected when a potential difference of about −1000V is applied in a second opposite direction. That is, the difference between the magnitudes of the two electrical property values is substantially zero (e.g., about 0 to about 3 nA). In other words, the two electrical property values are substantially equal, indicating the absence of a silver aggregate in the channel.

In contrast, in the presence of a silver aggregate in this example, the first and second electrical property values may be unequal, that is, substantially different. For example, when a silver aggregate is present in the channel (after introduction of both the silver-containing sample and TPEA2 into the channel), a first current value of about 43 nA to about 46 nA may be detected when a potential difference of about +1000 V is applied in a first direction, and a second current value of about −60 nA to about −63 nA may be detected when a potential difference of about −1000V is applied in a second opposite direction. That is, the difference between the magnitudes of the two electrical property values is non-zero. In other words, the two electrical property values are substantially unequal, indicating the presence of a silver aggregate in the channel.

In certain embodiments, the channel may be prepared for reuse for subsequent testing of samples. In step 784, a de-aggregation agent may be introduced into the channel using any suitable technique, for example, capillary filing or electro-kinetic filling. The de-aggregation agent may be selected so that interaction between the de-aggregation agent and the aggregate formed in the channel causes the aggregate to dissolve or disintegrate. The channel may be filled with an electrolyte buffer to flush out the channel and allow a sample and a sensor compound to be introduced into the channel. In one example, a channel including an aggregate may be prepared for reuse by washing the channel with dimethylsulfoxide introduced into the channel with a potential difference of about 500 V applied between the input and output nodes, followed by washing with about 10 mM sodium hydroxide introduced into the channel with a potential difference of about 500 V applied between the input and output nodes, followed by washing with about 1 M hydrogen chloride introduced into the channel with a potential difference of about 100 V applied between the input and output nodes. In another example, a channel including an aggregate may be prepared for reuse by washing the channel with dimethylsulfoxide introduced into the channel for about ten minutes with a potential difference of about 500 V applied between the input and output nodes, followed by washing with about 1 M hydrogen chloride introduced into the channel for about 10 minutes with a potential difference of about 100 V applied between the input and output nodes, followed by washing with about 100 mM sodium tetraborate introduced into the channel for about 10 minutes with a potential difference of about 500 V applied between the input and output nodes, followed by about 18 MILLIQ MEGAOHM water introduced into the channel for about 10 minutes with a potential difference of about 500 V applied between the input and output nodes.

In certain embodiments, in step 782, prior to disintegration of the aggregate, an absolute or relative concentration of silver ions may be determined based on an electrical property value of the channel. The concentration of silver ions may be determined in such a manner because the channels of exemplary detection systems have a high inner surface area to volume ratio. At low concentrations of silver ions, electrical conductivity in the channel is dominated by surface charges. As such, measurements of electrical properties of the channel can enable distinction between different ions. As a result, unique and sensitive measurements of the bulk flow in the channel can be used to determine information on the surface charges at the inner surface of the channel. Exemplary embodiments may thus compute predetermined ranges of electrical property values of the channel that are characteristic of silver ions given the dimensions of the channel and at different concentrations of silver ions. These predetermined values may then be used to determine an unknown concentration of silver ions in a sample.

Figure 9:
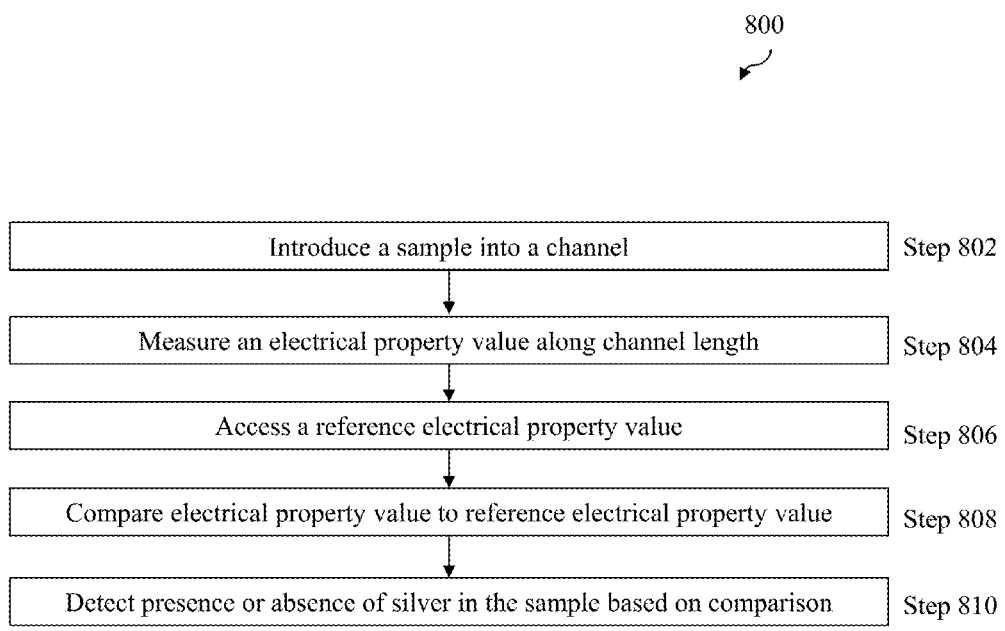

FIG. 9 is a flowchart illustrating a general exemplary method 800 for detecting the presence or absence of silver in a sample. In step 802, a sample may be introduced into a channel of a detection system, the channel having a length and a width, the length substantially greater than the width. In step 804, an electrical property value of an electrical property (e.g., current, conductivity, resistance) may be measured along at least a portion of the length of the channel after the sample is introduced into the channel. In step 806, a reference electrical property value may be accessed. The reference electrical property value may be associated with the electrical property detected in step 804 along at least a portion of the length of the channel prior to introduction of the sample into the channel. In step 808, the electrical property value measured in step 804 may be compared to the reference electrical property value accessed in step 806. In step 810, based on the comparison in step 808, presence or absence of silver in the sample may be determined.

Figure 10:
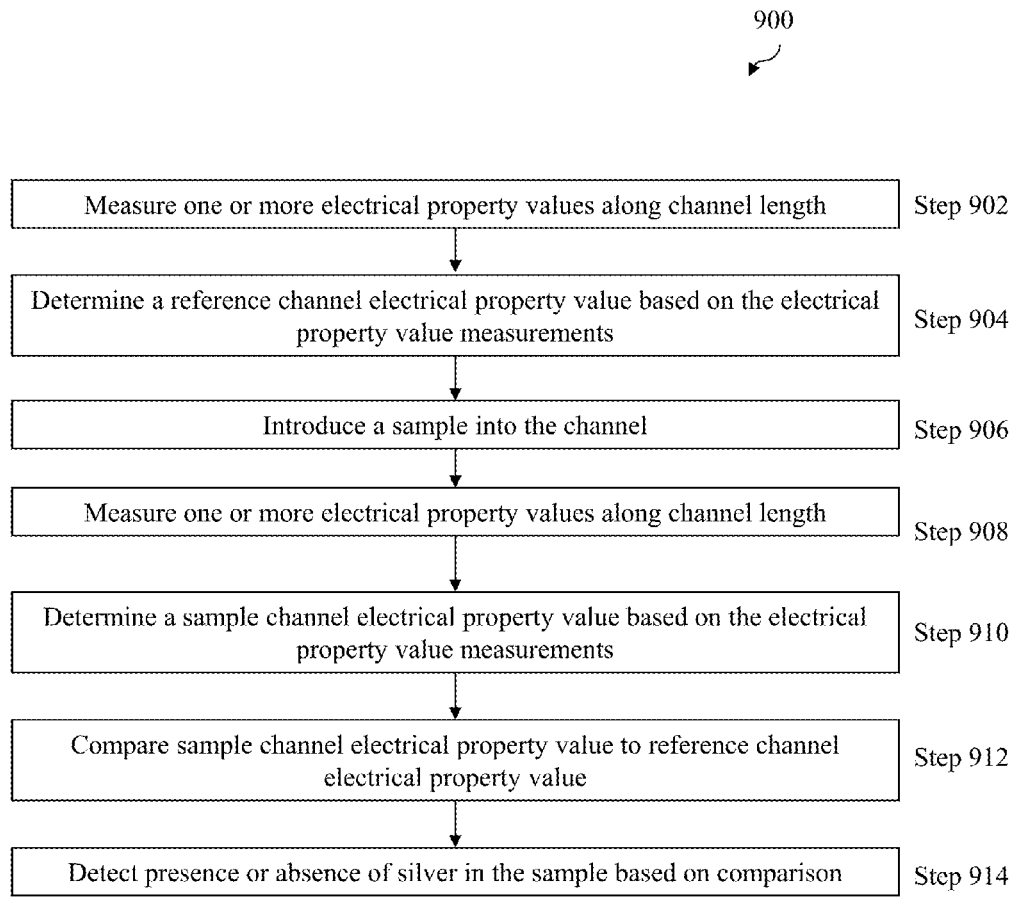

FIG. 10 is a flowchart illustrating a general exemplary method 900 for detecting the presence or absence of silver in a sample. In step 902, one or more electrical property values of one or more electrical properties (e.g., current, conductivity, resistance) may be measured along at least a portion of the length of a channel, the channel having a length and a width, the length substantially greater than the width. In step 904, a reference channel electrical property value may be determined based on the electrical property values of the channel measured in step 902. In step 906, a sample may be introduced into the channel. In step 908, one or more electrical property values of one or more electrical properties (e.g., current, conductivity, resistance) may be measured along at least a portion of the length of the channel after introduction of the sample into the channel. In step 910, a sample channel electrical property value may be determined based on the one or more electrical property values measured in step 908. In step 912, the sample channel electrical property value determined in step 910 may be compared to the reference channel electrical property value determined in step 904. In step 914, based on the comparison in step 912, presence or absence of silver in the sample may be determined.

Figure 11:
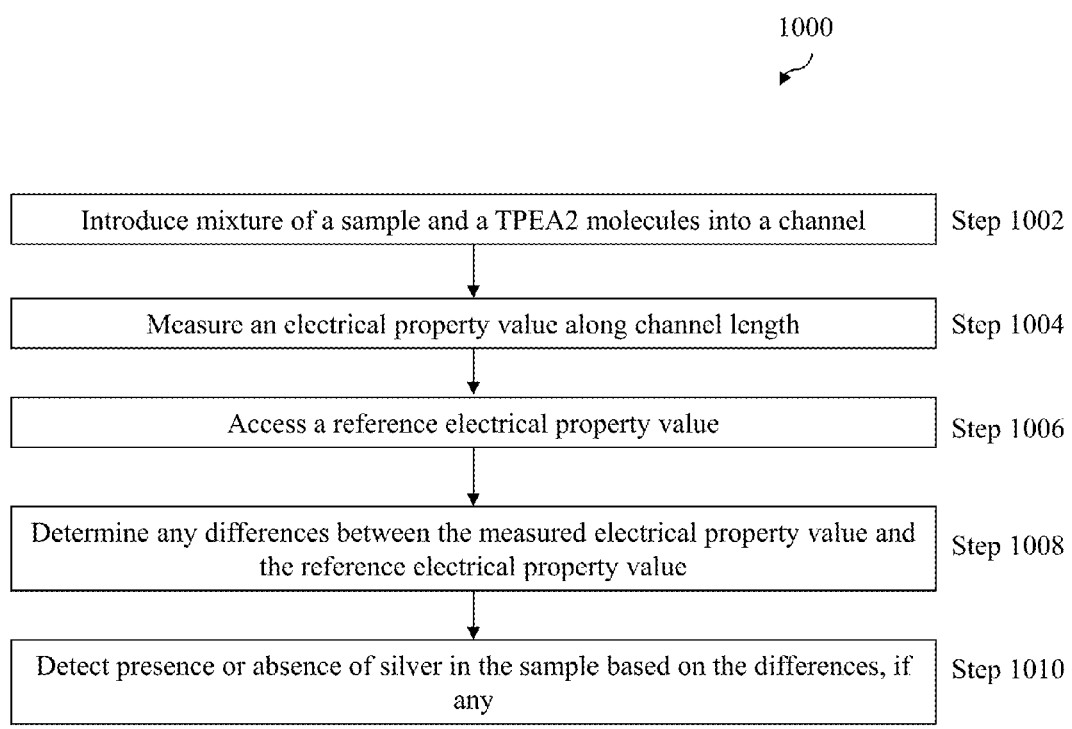

FIG. 11 is a flowchart illustrating a general exemplary method 1000 for detecting the presence or absence of silver in a sample. In step 1002, a mixture of a sample and a sensor compound may be introduced into a channel, the channel having a length and a width, the length substantially greater than the width. In step 1004, an electrical property value of an electrical property (e.g., current, conductivity, resistance) may be measured along at least a portion of the length of the channel after the sample and the sensor compound are introduced into the channel. In step 1006, a reference electrical property value may be accessed. The reference electrical property value may be associated with the electrical property detected in step 1004 along at least a portion of the length of the channel prior to introduction of the sample and the sensor compound into the channel. In step 1008, any differences between the electrical property value measured in step 1004 and the reference electrical property value accessed in step 1006 may be determined. In step 1010, based on the differences, if any, determined in step 1008, presence or absence of silver in the sample may be determined.

Figure 12:
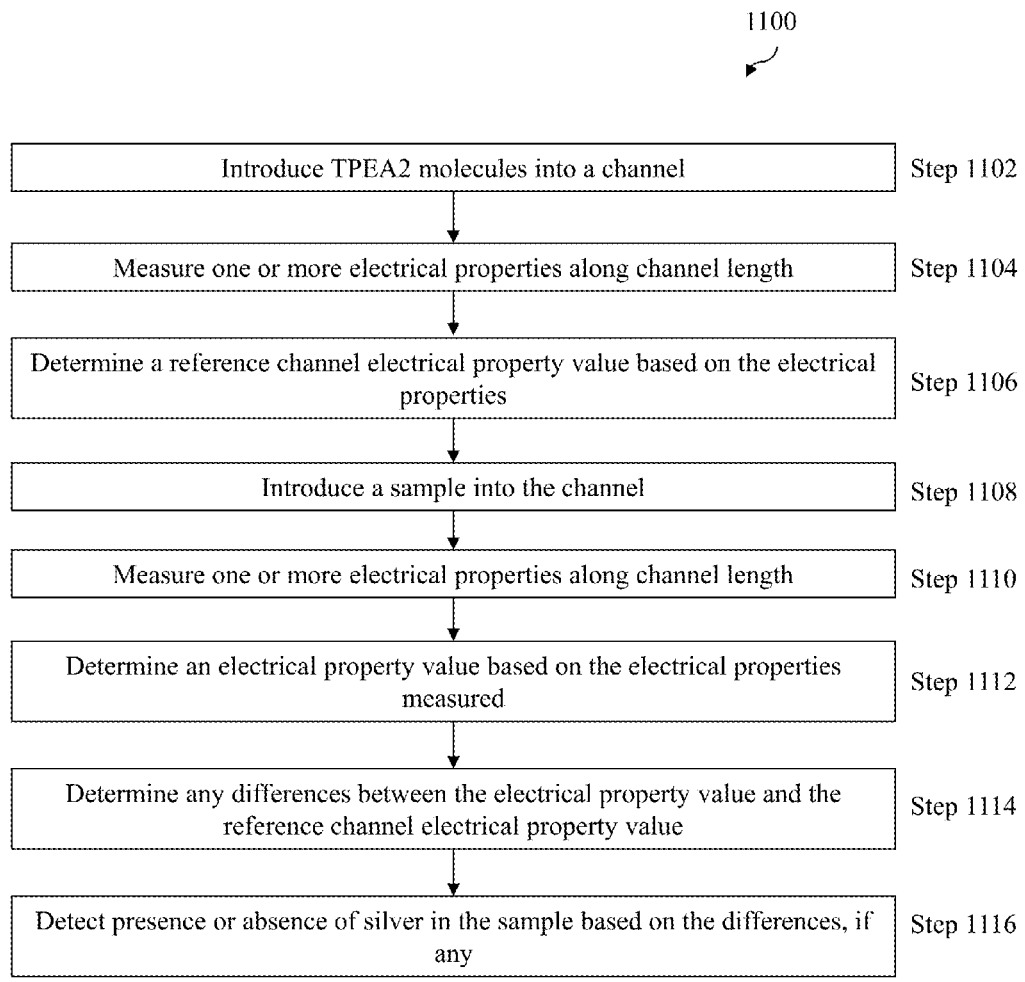

FIG. 12 is a flowchart illustrating a general exemplary method 1100 for detecting the presence or absence of silver in a sample. In step 1102, a sensor compound may be introduced into a channel, the channel having a length and a width, the length substantially greater than the width. In step 1104, one or more electrical properties (e.g., current, conductivity, resistance) may be measured along at least a portion of the length of a channel. In step 1106, a reference channel electrical property value may be determined based on the electrical properties of the channel measured in step 1104. In step 1108, a sample may be introduced into the channel. In step 1110, one or more electrical properties (e.g., current, conductivity, resistance) may be measured along at least a portion of the length of a channel. In step 1112, an electrical property value of the channel may be determined based on the one or more electrical properties measured in step 1110. In step 1114, any differences between the electrical property value determined in step 1112 and the reference channel electrical property value determined in step 1106 may be determined. In step 1116, based on the differences, if any, determined in step 1114, presence or absence of silver in the sample may be determined.

Figure 13:
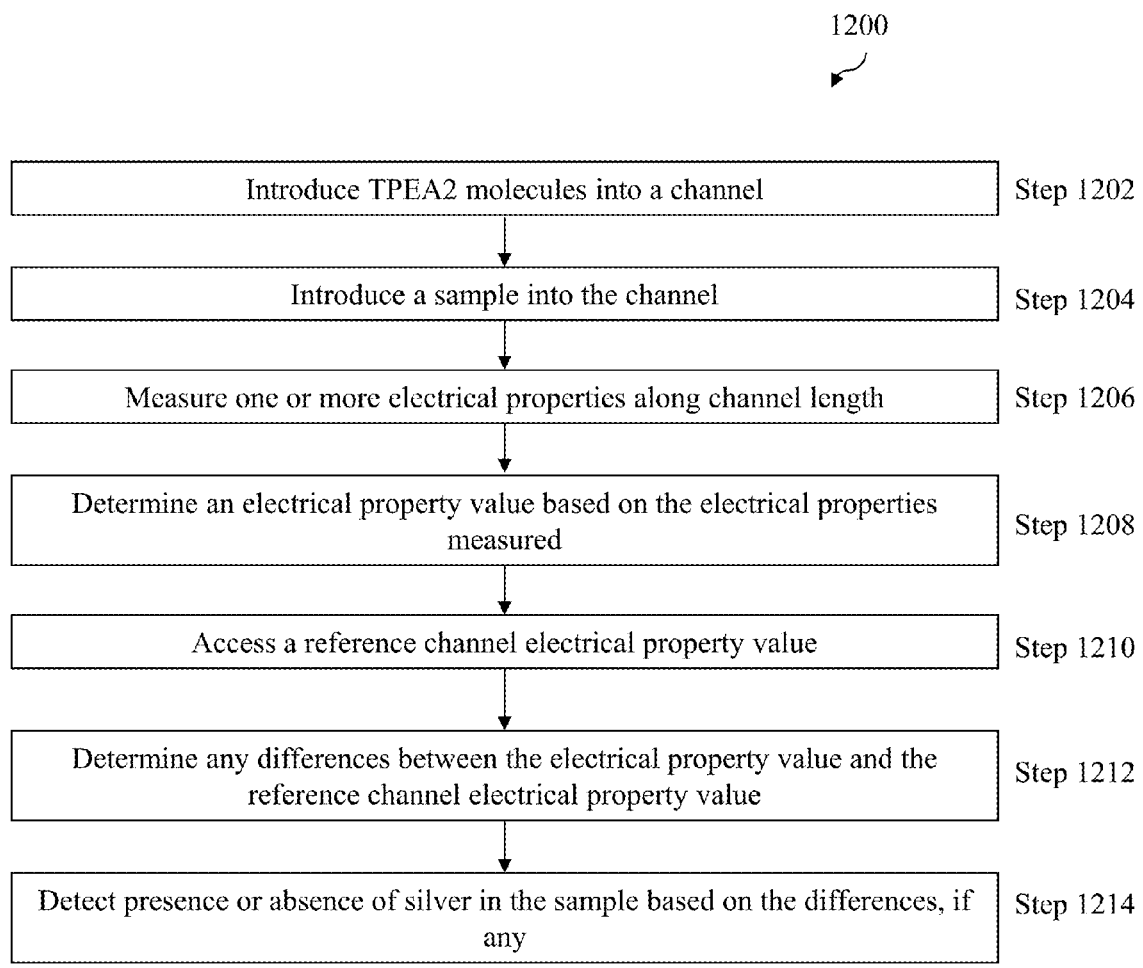

FIG. 13 is a flowchart illustrating a general exemplary method 1200 for detecting the presence or absence of silver in a sample. In step 1202, a sensor compound may be introduced into a channel, the channel having a length and a width, the length substantially greater than the width. In step 1204, a sample may be introduced into the channel. In step 1206, one or more electrical properties (e.g., current, conductivity, resistance) may be measured along at least a portion of the length of a channel. In step 1208, an electrical property value of the channel may be determined based on the one or more electrical properties measured in step 1206. In step 1210, a reference channel electrical property value may be accessed. The reference channel electrical property value may be measured prior to introduction of both the sensor compound and the sample into the channel. In step 1212, any differences between the electrical property value determined in step 1208 and the reference channel electrical property value accessed in step 1210 may be determined. In step 1214, based on the differences, if any, determined in step 1212, presence or absence of silver in the sample may be determined.

Figure 14:
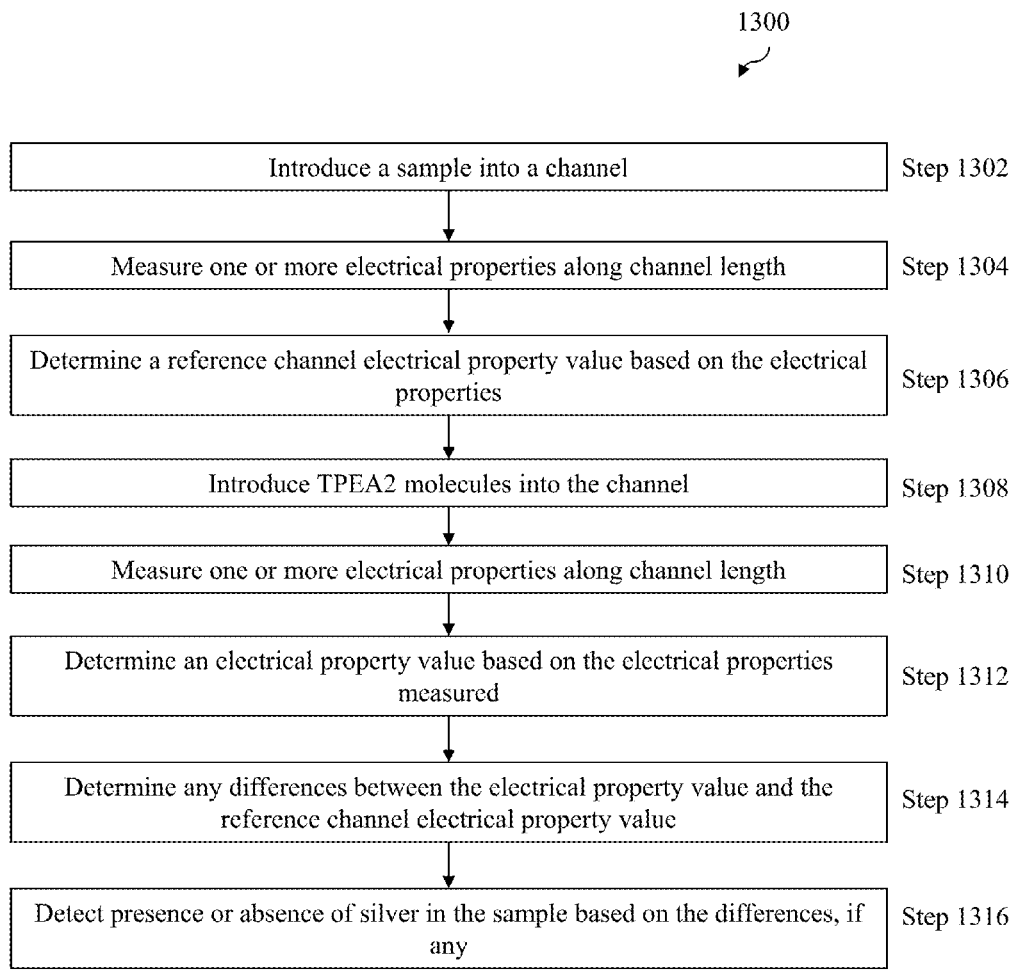

FIG. 14 is a flowchart illustrating a general exemplary method 1300 for detecting the presence or absence of silver in a sample. In step 1302, a sample may be introduced into a channel of a detection system, the channel having a length and a width, the length substantially greater than the width. In step 1304, one or more electrical properties (e.g., current, conductivity, resistance) may be measured along at least a portion of the length of the channel after the sample is introduced into the channel. In step 1306, a reference channel electrical property value may be determined based on the one or more electrical properties measured in step 1304. In step 1308, a sensor compound may be introduced into the channel. In step 1310, one or more electrical properties (e.g., current, conductivity, resistance) may be measured along at least a portion of the length of the channel after the sensor compound is introduced into the channel. In step 1312, an electrical property value may be determined based on the one or more electrical properties measured in step 1310 after the sensor compound and the sample are introduced into the channel. In step 1314, any differences between the electrical property value determined in step 1312 and the reference channel electrical property value determined in step 1306 may be determined. In step 1316, based on the differences, if any, determined in step 1314, presence or absence of silver in the sample may be determined.

Figure 15:
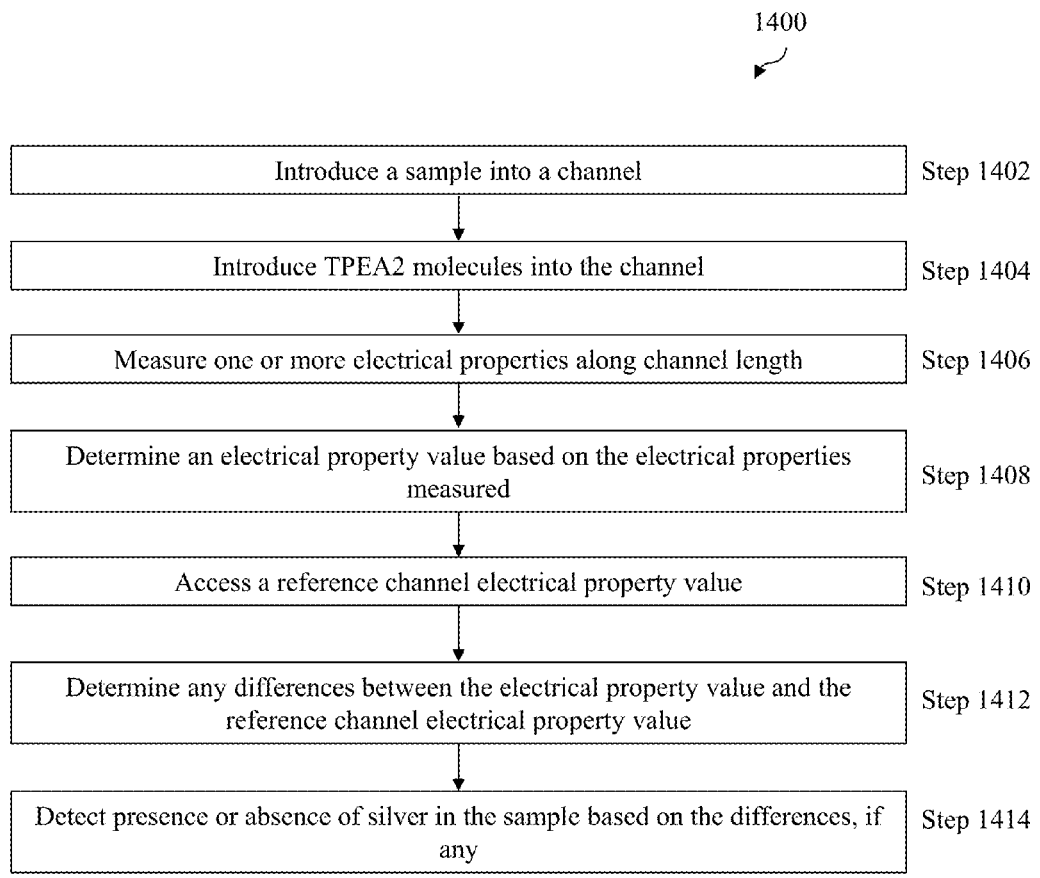

FIG. 15 is a flowchart illustrating a general exemplary method 1400 for detecting the presence or absence of silver in a sample. In step 1402, a sample may be introduced into a channel of a detection system, the channel having a length and a width, the length substantially greater than the width. In step 1404, a sensor compound may be introduced into the channel. In step 1406, one or more electrical properties (e.g., current, conductivity, resistance) may be measured along at least a portion of the length of the channel after the sample and the sensor compound are introduced into the channel. In step 1408, an electrical property value may be determined based on the one or more electrical properties measured in step 1406 after the sensor compound and the sample are introduced into the channel. In step 1410, a reference channel electrical property value may be accessed. The reference channel electrical property value may be measured prior to introduction of both the sensor compound and the sample into the channel. In step 1412, any differences between the electrical property value determined in step 1408 and the reference channel electrical property value accessed in step 1410 may be determined. In step 1414, based on the differences, if any, determined in step 1412, presence or absence of silver in the sample may be determined.

Figure 16:
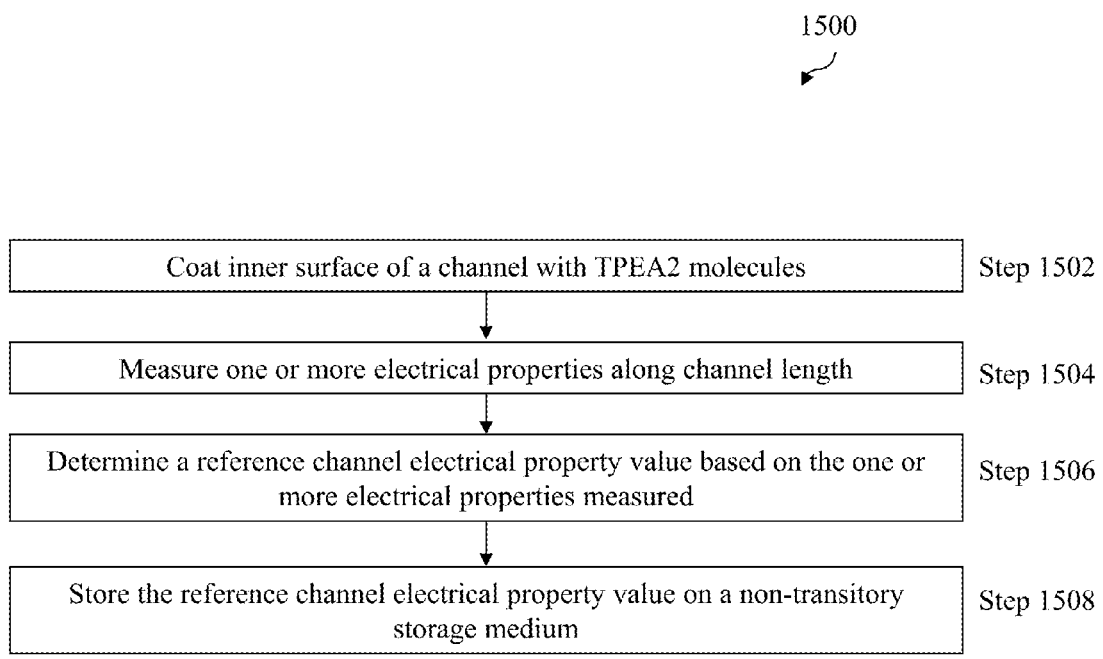

FIG. 16 is a flowchart illustrating a general exemplary method 1500 for detecting the presence or absence of silver in a sample. In step 1502, at least a portion of an inner surface of a channel may be coated with a sensor compound. The channel may have a length and a width, the length substantially greater than the width. In some cases, the inner portion of the channel may be pre-treated or covalently modified to enable specific covalent attachment of the sensor compound to the inner surface and to prevent non-specific attachment of other molecules to the inner surface. In step 1504, one or more electrical properties (e.g., current, conductivity, resistance) may be measured along at least a portion of the length of a channel. In step 1506, a reference channel electrical property value may be determined based on the one or more electrical properties measured in step 1504. In step 1508, the reference channel electrical property value may be stored on a non-transitory storage medium for use in determining whether silver is present or absent in the sample.

IV. Exemplary Processors and Computing Devices

Systems and methods disclosed herein may include one or more programmable processors, processing units and computing devices having associated therewith executable computer-executable instructions held or encoded on one or more non-transitory computer readable media, RAM, ROM, hard drive, and/or hardware. In exemplary embodiments, the hardware, firmware and/or executable code may be provided, for example, as upgrade module(s) for use in conjunction with existing infrastructure (for example, existing devices/processing units). Hardware may, for example, include components and/or logic circuitry for executing the embodiments taught herein as a computing process.

Displays and/or other feedback means may also be included, for example, for rendering a graphical user interface, according to the present disclosure. The displays and/or other feedback means may be stand-alone equipment or may be included as one or more components/modules of the processing unit(s).

The actual computer-executable code or control hardware that may be used to implement some of the present embodiments is not intended to limit the scope of such embodiments. For example, certain aspects of the embodiments described herein may be implemented in code using any suitable programming language type such as, for example, the MATLAB technical computing language, the LABVIEW graphical programming language, assembly code, C, C# or C++ using, for example, conventional or object-oriented programming techniques. Such computer-executable code may be stored or held on any type of suitable non-transitory computer-readable medium or media, such as, a magnetic or optical storage medium.

As used herein, a "processor," "processing unit," "computer" or "computer system" may be, for example, a wireless or wire line variety of a microcomputer, minicomputer, server, mainframe, laptop, personal data assistant (PDA), wireless e-mail device (for example, "BlackBerry," "Android" or "Apple," trade-designated devices), cellular phone, pager, processor, fax machine, scanner, or any other programmable device configured to transmit and receive data over a network. Computer systems disclosed herein may include memory for storing certain software applications used in obtaining, processing and communicating data. It can be appreciated that such memory may be internal or external to the disclosed embodiments. The memory may also include a non-transitory storage medium for storing computer-executable instructions or code, including a hard disk, an optical disk, floppy disk, ROM (read only memory), RAM (random access memory), PROM (programmable ROM), EEPROM (electrically erasable PROM), flash memory storage devices, or the like.

Figure 17:
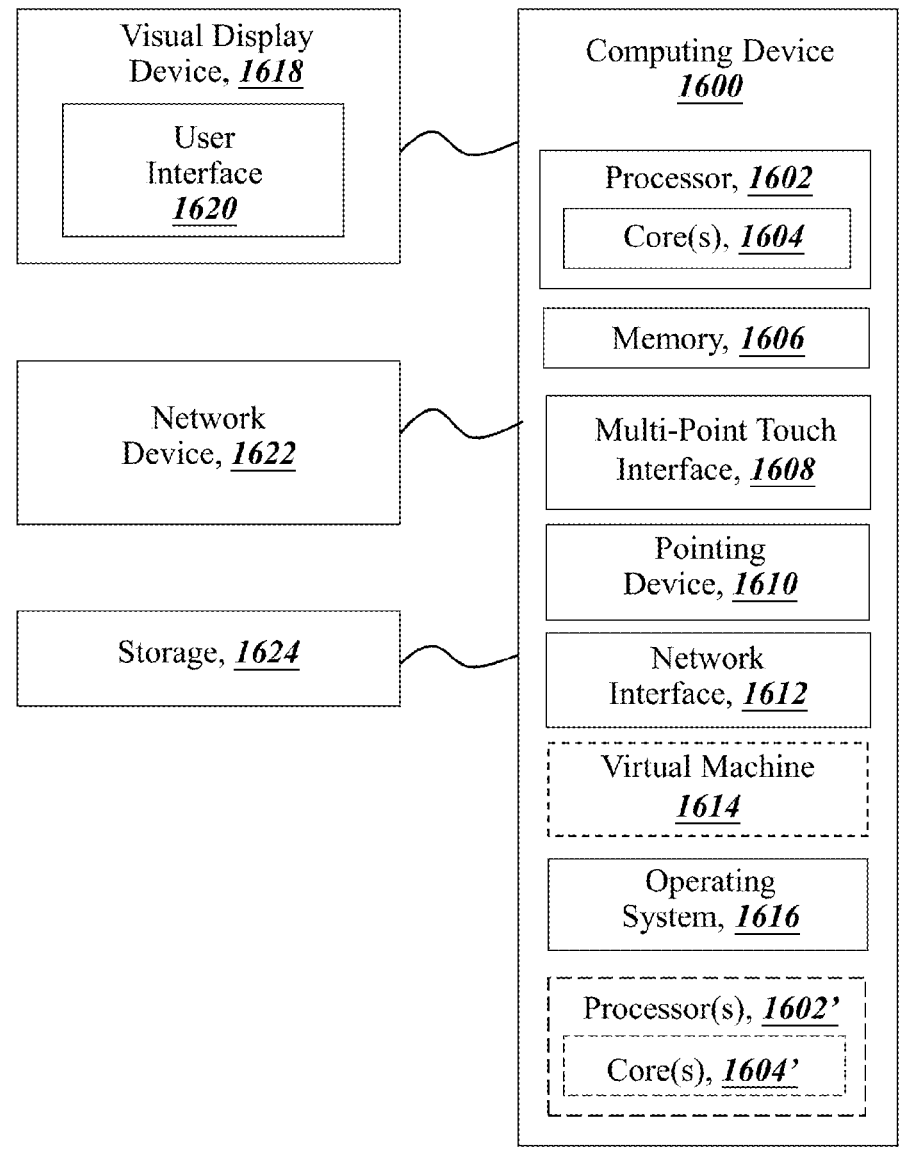
FIG. 17 is a block diagram of an exemplary processing or computing device that may be used to implement and execute exemplary computer-executable methods.

FIG. 17 depicts a block diagram representing an exemplary computing device 1600 that may be used to implement the systems and methods disclosed herein. In certain embodiments, the processor 130 illustrated in FIG. 1 may be configured as or may implement certain functionality and/or components of the computing device 1600. In certain embodiments, the silver detection circuit may be configured as or may implement certain functionality and/or components of the computing device 1600.

The computing device 1600 may be any computer system, such as a workstation, desktop computer, server, laptop, handheld computer, tablet computer (e.g., the iPad™ tablet computer), mobile computing or communication device (e.g., the iPhone™ mobile communication device, the Android™ mobile communication device, and the like), or other form of computing or telecommunications device that is capable of communication and that has sufficient processor power and memory capacity to perform the operations described herein. In exemplary embodiments, a distributed computational system may include a plurality of such computing devices.

The computing device 1600 may include one or more non-transitory computer-readable media having encoded thereon one or more computer-executable instructions or software for implementing the exemplary methods described herein. The non-transitory computer-readable media may include, but are not limited to, one or more types of hardware memory and other tangible media (for example, one or more magnetic storage disks, one or more optical disks, one or more USB flash drives), and the like. For example, memory 1606 included in the computing device 1600 may store computer-readable and computer-executable instructions or software for implementing functionality of a silver detection circuit 122 as described herein. The computing device 1600 may also include processor 1602 and associated core 1604, and in some embodiments, one or more additional processor(s) 1602' and associated core(s) 1604' (for example, in the case of computer systems having multiple processors/cores), for executing computer-readable and computer-executable instructions or software stored in the memory 1602 and other programs for controlling system hardware. Processor 1602 and processor(s) 1602' may each be a single core processor or a multiple core (1604 and 1604') processor.

Virtualization may be employed in the computing device 1600 so that infrastructure and resources in the computing device may be shared dynamically. A virtual machine 1614 may be provided to handle a process running on multiple processors so that the process appears to be using only one computing resource rather than multiple computing resources. Multiple virtual machines may also be used with one processor.

Memory 1606 may include a non-transitory computer system memory or random access memory, such as DRAM, SRAM, EDO RAM, and the like. Memory 1606 may include other types of memory as well, or combinations thereof.

A user may interact with the computing device 1600 through a visual display device 1618, such as a screen or monitor, which may display one or more graphical user interfaces 1620 provided in accordance with exemplary embodiments described herein. The visual display device 1618 may also display other aspects, elements and/or information or data associated with exemplary embodiments. In certain cases, the visual display device 1618 may display value of one or more electrical properties detected in an exemplary silver detection system or method. In certain cases, the visual display device 1618 may display an indication of whether a sample contains or does not contain silver. In certain embodiments, other types of interfaces may be provided to communicate the same information, for example, a sound alarm that may be activated if silver is determined to be present in a sample.

The computing device 1600 may include other I/O devices for receiving input from a user, for example, a keyboard or any suitable multi-point touch interface 1608 or pointing device 1610 (e.g., a mouse, a user's finger interfacing directly with a display device). As used herein, a "pointing device" is any suitable input interface, specifically, a human interface device, that allows a user to input spatial data to a computing system or device. In an exemplary embodiment, the pointing device may allow a user to provide input to the computer using physical gestures, for example, pointing, clicking, dragging, dropping, and the like. Exemplary pointing devices may include, but are not limited to, a mouse, a touchpad, a finger of the user interfacing directly with a display device, and the like.

The keyboard 1608 and the pointing device 1610 may be coupled to the visual display device 1618. The computing device 1600 may include other suitable conventional I/O peripherals. The I/O devices may facilitate implementation of the one or more graphical user interfaces 1620, for example, implement one or more of the graphical user interfaces described herein.

The computing device 1600 may include one or more storage devices 1624, such as a durable disk storage (which may include any suitable optical or magnetic durable storage device, e.g., RAM, ROM, Flash, USB drive, or other semiconductor-based storage medium), a hard-drive, CD-ROM, or other computer readable media, for storing data and computer-readable instructions and/or software that implement exemplary embodiments as taught herein. In exemplary embodiments, the one or more storage devices 1624 may provide storage for data that may be generated by the systems and methods of the present disclosure. The one or more storage devices 1624 may be provided on the computing device 1600 and/or provided separately or remotely from the computing device 1600.

The computing device 1600 may include a network interface 1612 configured to interface via one or more network devices 1622 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 1612 may include a built-in network adapter, network interface card, PCMCIA network card, card bus network adapter, wireless network adapter, USB network adapter, modem or any other device suitable for interfacing the computing device 1600 to any type of network capable of communication and performing the operations described herein. The network device 1622 may include one or more suitable devices for receiving and transmitting communications over the network including, but not limited to, one or more receivers, one or more transmitters, one or more transceivers, one or more antennae, and the like.

The computing device 1600 may run any operating system 1616, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, any operating systems for mobile computing devices, or any other operating system capable of running on the computing device and performing the operations described herein. In exemplary embodiments, the operating system 1616 may be run in native mode or emulated mode. In an exemplary embodiment, the operating system 1616 may be run on one or more cloud machine instances.

One of ordinary skill in the art will recognize that exemplary computing device 1600 may include more or fewer modules than those shown in FIG. 17.

In describing exemplary embodiments, specific terminology is used for the sake of clarity. For purposes of description, each specific term is intended to, at least, include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by $\frac{1}{20}$th, $\frac{1}{10}$th, $\frac{1}{5}$th, $\frac{1}{3}$rd, $\frac{1}{2}$nd, and the like, or by rounded-off approximations thereof, unless otherwise specified. Moreover, while exemplary embodiments have been shown and described with references to particular embodiments thereof, those of ordinary skill in the art will understand that various substitutions and alterations in form and details may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than shown.

Blocks of the block diagram and the flow chart illustrations support combinations of means for performing the specified functions, combinations of steps for performing the specified functions and program instruction means for performing the specified functions. It will also be understood that some or all of the blocks/steps of the circuit diagram and process flowchart, and combinations of the blocks/steps in the circuit diagram and process flowcharts, can be implemented by special purpose hardware-based computer systems that perform the specified functions or steps, or combinations of special purpose hardware and computer instructions. Exemplary systems may include more or fewer modules than those illustrated in the exemplary block diagrams.

Many modifications, combinations and other embodiments of the inventions set forth herein will come to mind to one skilled in the art to which these embodiments of the invention pertain having the benefit of the teachings presented in the foregoing descriptions and the associated drawings. Therefore, it is to be understood that the embodiments of the invention are not to be limited to the specific embodiments disclosed and that modifications, combinations and other embodiments are intended to be included within the scope of the appended claims. Although specific terms are employed herein, they are used in a generic and descriptive sense only and not for purposes of limitation.

What is claimed is:
1. A method for detecting the presence or absence of silver ions in a sample, the method comprising:
   introducing a sample into a channel having an inner space disposed between a first and a second electrode, the channel having a length and a width, the length substantially greater than the width;
   obtaining a applying a potential difference across the length of the channel while measured electrical property by measuring an electrical property value of an electrical property along at least a portion of the length of the channel after the sample is introduced into the channel;
   accessing a reference electrical property value, the reference electrical property value associated with an electrical property of the channel along at least a portion of the length of the channel prior to introduction of the sample into the channel;
   comparing the measured electrical property value and the reference electrical property value;
   wherein in the inner space of the channel there is an interaction between silver ions and a sensor composition comprising TPEA2 and sodium tetraborate, wherein the sensor composition is allowed to flow along the length of the channel, and wherein the TPEA2 has the following structure:

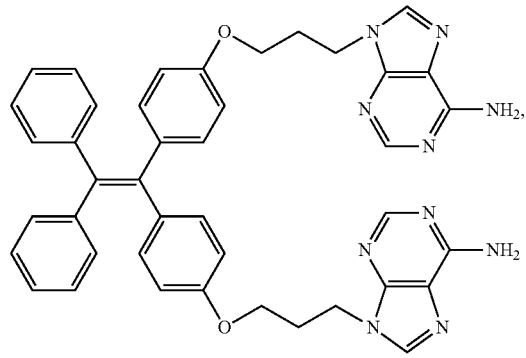 [SMILES: Nc1ncnc2c1ncn2CCCOc1ccc(C(=C(c2ccccc2)c2ccccc2)c2ccc(OCCCn3cnc4c(N)ncnc43)cc2)cc1]

thereby determining whether silver ions are present in the channel.

2. The method of claim 1, further comprising:
   prior to introducing the sample into the channel, measuring one or more electrical properties of the channel along at least the portion of the length of the channel; and
   determining the reference electrical property value based on the one or more electrical properties of the channel measured during the measuring one or more electrical properties of the channel along at least the portion of the length of the channel.

3. The method of claim 1, further comprising:
   introducing the TPEA2 into the channel prior to measuring the electrical property value of the electrical property along at least the portion of the length of the channel.

4. The method of claim 1, further comprising:
   waiting for an adjustment time period between introducing the sample into the channel and measuring the electrical property value.

5. The method of claim 1, further comprising:
   displaying, on a visual display device, an indication of whether silver ions are present in the sample.

6. The method of claim 1, wherein the measured electrical property value corresponds to a value of an electrical current conducted along at least the portion of length of the channel or to an electrical conductivity along at least the portion of the length of the channel.

7. The method of claim 1, wherein the channel is configured to have a length ranging from 10 nanometers to 10 centimeters.

8. The method of claim 1, wherein the channel is configured to have a width ranging from 1 nanometer to 50 microns.

9. The method of claim 1, wherein the channel is configured to have a depth ranging from 1 nanometer to 1 micron.

10. The method of claim 1, further comprising:
    monitoring a first set of one or more values of the electrical property in the channel during a first time period, and a second set of one or more values of the electrical property in the channel during a second time period;
    selecting the reference electrical property value from the first set of values upon equilibration of the one or more values in the channel during the first time period; and
    selecting the measured electrical property value from the second set of values upon equilibration of the one or more values in the channel during the second time period.

11. The method of claim 1, wherein substantially unequal reference and measured electrical property values are indicative of the presence of silver ions.

12. The method of claim 1, wherein substantially equal reference and measured electrical property values are indicative of the absence of silver ions.

13. The method of claim 1, wherein the sample and the TPEA2 are introduced into the inner space concurrently.

14. The method of claim 1, wherein the sample and the TPEA2 are introduced into the inner space sequentially.

15. A method for detecting the presence or absence of silver ions in a sample, the method comprising:

introducing a sensor composition comprising TPEA2 and sodium tetraborate into a channel having an inner space disposed between a first and a second electrode, the channel having a length and a width, the length being substantially greater than the width, wherein the sensor composition is allowed to flow along the length of the channel, and wherein the TPEA2 has the following structure:

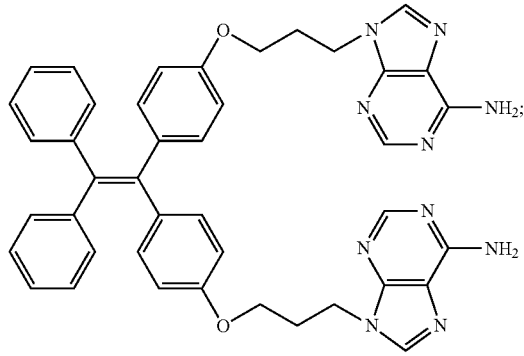 [SMILES: Nc1ncnc2c1ncn2CCCOc1ccc(C(=C(c2ccccc2)c2ccccc2)c2ccc(OCCCn3cnc4c(N)ncnc43)cc2)cc1]

measuring one or more electrical properties of the channel along at least a portion of the length of the channel;

determining a reference channel electrical property value based on the one or more electrical properties of the channel measured during the previous measuring step;

introducing a sample into the channel;

measuring the one or more electrical properties of the channel along at least the portion of the length of the channel after the sample and the sensor composition are introduced into the channel;

determining an electrical property value based on the one or more electrical properties measured after the sensor composition and the sample are introduced into the channel;

determining any differences between the reference channel electrical property value and the electrical property value;

wherein in the inner space of the channel there is an interaction between silver ions and the sensor composition, thereby determining whether silver ions are present in the channel.

16. A method for detecting the presence or absence of silver ions in a sample, the method comprising:

introducing a sample and a sensor composition comprising TPEA2 and sodium tetraborate into a channel having an inner space disposed between a first and a second electrode, the channel having a length and a width, the length substantially greater than the width, wherein the sensor composition is allowed to flow along the length of the channel, and wherein the TPEA2 has the following structure:

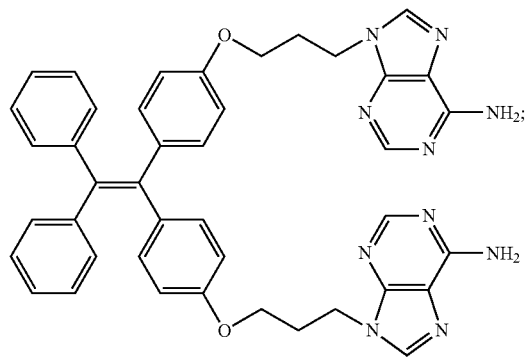 [SMILES: Nc1ncnc2c1ncn2CCCOc1ccc(C(=C(c2ccccc2)c2ccccc2)c2ccc(OCCCn3cnc4c(N)ncnc43)cc2)cc1]

applying a first potential difference across the length of the channel in a first direction along the length of the channel;

measuring a first electrical property value of an electrical property along at least a portion of the length of the channel while the first potential difference is applied;

applying a second potential difference across the length of the channel in a second direction along the length of the channel, the second direction opposite to the first direction;

measuring a second electrical property value of the electrical property along at least the portion of the length of the channel while the second potential difference is applied;

comparing the first and second electrical property values;

wherein in the inner space of the channel there is an interaction between silver ions and the sensor composition, thereby determining whether silver ions are present in the channel.

17. The method of claim 16, wherein the first and second electrical property values correspond to electrical current values conducted along at least the portion of length of the channel or to electrical conductivity values along at least the portion of the length of the channel.

* * * * *

UNITED STATES PATENT AND TRADEMARK OFFICE
CERTIFICATE OF CORRECTION

PATENT NO. : 10,352,899 B2
APPLICATION NO. : 14/507820
DATED : July 16, 2019
INVENTOR(S) : Sumita Pennathur Page 1 of 1

It is certified that error appears in the above-identified patent and that said Letters Patent is hereby corrected as shown below:

On the Title Page

On Page 3, Column 2, Item (56), Line 31, under Other Publications, delete "Quantative" and insert --Quantitative--.

On Page 3, Column 2, Item (56), Line 41, under Other Publications, delete "Biphys" and insert --Biophys--.

On Page 3, Column 2, Item (56), Line 66, under Other Publications, delete "Bioeletronics" and insert --Bioelectronics--.

In the Specification

In Column 12, Line 12, delete "tricholorsilane," and insert --richlorosilane,--.

In Column 12, Line 32, delete "op1." and insert --opl.--.

In Column 20, Line 39, delete "tricholorsilane," and insert --trichlorosilane,--.

In Column 21, Line 6, delete "SEL" and insert --µL--.

In Column 31, Line 25, delete "Kiethley" and insert --Keithley--.

In the Claims

In Column 43, Lines 46-47, Claim 1, after "obtaining a" delete "applying a potential difference across the length of the channel while".

In Column 43, Line 49 (approx.), Claim 1, after "by" insert --applying a potential difference across the length of the channel while--.

Signed and Sealed this
Twenty-second Day of October, 2019

Andrei Iancu
*Director of the United States Patent and Trademark Office*